United States Patent [19]
Sine et al.

[11] Patent Number: 5,972,359
[45] Date of Patent: Oct. 26, 1999

[54] SKIN CARE COMPOSITIONS AND METHOD OF IMPROVING SKIN APPEARANCE

[75] Inventors: Mark Richard Sine; James Pedrosa SaNogueira, Jr.; Nancy Coultrip Dawes, all of Cincinnati, Ohio

[73] Assignee: The Procter & Gamble Company, Cincinnati, Ohio

[21] Appl. No.: 09/061,509

[22] Filed: Apr. 17, 1998

Related U.S. Application Data

[63] Continuation-in-part of application No. 08/862,775, May 23, 1997, abandoned.

[51] Int. Cl.$^6$ .............................. A61K 7/00; A61K 7/42; A61K 7/021; C09C 1/36
[52] U.S. Cl. ........................ 424/401; 106/428; 106/436; 424/59; 424/60; 424/63; 424/400; 514/847; 514/938
[58] Field of Search .................. 424/59, 60, 63, 424/400, 401; 514/847, 938; 106/428, 436

[56] References Cited

U.S. PATENT DOCUMENTS

| | | | |
|---|---|---|---|
| 3,861,946 | 1/1975 | Waitkins et al. | 117/100 B |
| 5,082,660 | 1/1992 | Ounanian et al. | 424/63 |
| 5,188,831 | 2/1993 | Nicoll et al. | 424/401 |
| 5,215,580 | 6/1993 | Elfenthal et al. | 106/441 |
| 5,223,250 | 6/1993 | Mitchell et al. | 424/59 |
| 5,223,559 | 6/1993 | Arraudeau et al. | 524/47 |
| 5,366,660 | 11/1994 | Tapley | 252/309 |
| 5,468,471 | 11/1995 | Zecchino et al. | 424/59 |
| 5,531,985 | 7/1996 | Mitchell et al. | 424/59 |
| 5,587,148 | 12/1996 | Mitchell et al. | 424/59 |
| 5,618,522 | 4/1997 | Kaleta et al. | 424/60 |
| 5,643,555 | 7/1997 | Collin et al. | 424/59 |
| 5,693,329 | 12/1997 | Marchi-Lemann et al. | 424/401 |
| 5,700,451 | 12/1997 | Yue et al. | 424/59 |
| 5,733,531 | 3/1998 | Mitchnick et al. | 424/59 |

FOREIGN PATENT DOCUMENTS

| | | |
|---|---|---|
| 0 293 795 A1 | 12/1988 | European Pat. Off. . |
| 0 502 769 A1 | 9/1992 | European Pat. Off. . |
| 245815 A1 | 5/1987 | Germany . |
| 7-330536 | 12/1995 | Japan . |
| 8-073316 | 3/1996 | Japan . |
| 8-073317 | 3/1996 | Japan . |
| 1112193 | 5/1965 | United Kingdom . |
| 94/09756 | 5/1994 | WIPO . |
| 96/07396 A2 | 3/1996 | WIPO . |

OTHER PUBLICATIONS

Derwent Abstract No. 92–302056/37; Date Sep. 9, 1992; Country Europe (abstract of Doc. #10 above).
"Quantification of the Soft–Focus Effect," Emmert, Dr. Ralf, *Cosmetics & Toiletries*, vol. 111, Jul. 1996, pp. 57–61.
Chemical Abstract No. 94–188862/23; Date Oct. 20, 1992; Country Japan (abstract of JP 06–128,122 A).
Chemical Abstract No. 96–388694/39; Date Jan. 9, 1995; Country Japan (abstract of JP 08–188,723 A).

*Primary Examiner*—Shelley A. Dodson
*Attorney, Agent, or Firm*—George W. Allen; Armina E. Matthews; Loretta J. Henderson

[57] ABSTRACT

Disclosed are topical compositions which provide good coverage of skin imperfections, e.g., pores and uneven skin tone, while retaining a natural skin appearance. The compositions contain a particulate material having a refractive index of at least about 2, e.g., $TiO_2$.

23 Claims, No Drawings

SKIN CARE COMPOSITIONS AND METHOD OF IMPROVING SKIN APPEARANCE

This is a CIP of application Ser. No. 08/862,775 filed May 23, 1997 now abandoned.

TECHNICAL FIELD

The present invention relates to the field of topical compositions for improving the appearance or other condition of skin. More particularly, the invention relates to topical compositions which provide good coverage of skin imperfections, e.g., pores and uneven skin tone, while retaining a natural skin appearance.

BACKGROUND

A variety of compounds have been described in the art as being useful for regulating fine lines, wrinkles and other forms of undesirable skin surface texture. In addition, Vitamin $B_3$ compounds, particularly niacinamide, have recently been found to provide measurable benefits in regulating skin condition, including regulating fine lines, wrinkles and other forms of uneven or rough surface texture associated with aged or photodamaged skin. However, many materials require multiple applications over an extended period to provide such appearance benefits. It would be advantageous to provide a topical composition which provides a more immediate improvement in the appearance of fine lines, wrinkles, pores and other forms of undesirable skin surface texture.

Particulate materials, including $TiO_2$, have been included in skin care compositions. For example, emulsions may contain $TiO_2$ as an opacifying agent to provide a white appearance to the emulsion. Commercial sunscreening compositions may employ such particulates to impart a sunscreening effect. Several publications have also disclosed the use of $TiO_2$ in skin care compositions. See, e.g., U.S. Pat. No. 5,223,559 and patent application Nos. DE 245815, WO 94/09756 and JP 08188723. In addition, R. Emmert has stated the desire to use optical means to formulate products that give the consumer an immediate, visual improvement (Dr. Ralf Emmert, Quantification of the Soft-Focus Effect, Cosmetics & Toiletries, Vol. 111, July 1996, pp. 57–61). Emmert discloses that one can mechanically fill in skin lines with a reflective substance such as $TiO_2$. However, Emmert teaches that such reflective materials result in an undesirable mask-like appearance, and that one should therefore use a material that diffuses light yet is sufficiently transparent to avoid the mask-like appearance.

Previous topical compositions containing reflective materials such as $TiO_2$, of which the present inventors are aware, either do not provide coverage sufficient to reduce the appearance of skin imperfections, or tend to result in unacceptable skin whitening or other unnatural appearance when applied to the skin. It has also now been found that materials which primarily diffuse light, rather than reflect light, do not provide good coverage of skin imperfections when used in amounts which are esthetically acceptable to consumers. More particularly, when used at relatively high concentrations to provide coverage, these materials suffer from unacceptable skin whitening.

The present inventors have now found that reflective materials such as $TiO_2$ can be formulated in topical compositions to provide good coverage of skin imperfections while retaining a generally natural appearance, e.g., without unacceptable skin whitening. The compositions are especially suitable for providing an immediate visual improvement in skin appearance.

It is an object of the present invention to provide topical compositions suitable for imparting an essentially immediate visual improvement in skin appearance. It is another object of the present invention to provide topical compositions containing a reflective particulate material, e.g., $TiO_2$, which provide desirable coverage of skin imperfections such as pores and uneven skin tone, while maintaining a natural skin appearance (e.g., without unacceptable skin whitening). Another object of the present invention is to provide such topical compositions which are additionally useful for regulating skin appearance and/or condition, especially regulating textural or tonal discontinuities in skin (e.g., pores and uneven skin color).

The present invention also relates to methods of improving skin appearance and/or condition by topical application of the subject compositions.

These and other objects of this invention will become apparent in light of the following disclosure.

SUMMARY OF THE INVENTION

The present invention relates to topical compositions comprising a particulate material and a topical carrier, the particulate material having a refractive index of at least about 2 and a neat primary particle size of from about 100 nm to about 300 nm. The composition preferably contains from about 0.3% to about 2% of the particulate material. Preferred particulates are selected from $TiO_2$, ZnO, and ZrO, with $TiO_2$ being more preferred. The compositions are useful for imparting an essentially immediate visual improvement in skin appearance, while maintaining a natural skin appearance. Compositions of the invention are characterized by their contrast ratio and % transmittance or Coverage Index. Compositions of the invention have a contrast ratio of from about 9 to about 30 and a % transmittance of from about 92% to about 62%. Preferred compositions can be further characterized by their apparent viscosity and Hydration Factor.

DETAILED DESCRIPTION OF THE INVENTION

All percentages and ratios used herein are by weight of the total composition and all measurements made are at 25° C., unless otherwise designated.

The compositions of the present invention can comprise, consist essentially of, or consist of, the essential as well as optional ingredients and components described herein. As used herein, "consisting essentially of" means that the composition or component may include additional ingredients, but only if the additional ingredients do not materially alter the basic and novel characteristics of the claimed compositions or methods.

All publications cited herein are hereby incorporated by reference in their entirety.

The term "topical application", as used herein, means to apply or spread the compositions of the present invention onto the surface of the skin.

The term "dermatologically-acceptable," as used herein, means that the compositions or components thereof so described are suitable for use in contact with human skin without undue toxicity, incompatibility, instability, allergic response, and the like.

The term "safe and effective amount" as used herein means an amount of a compound, component, or composition sufficient to significantly induce a positive benefit, preferably a positive skin appearance or feel benefit, including independently the benefits disclosed herein, but low enough to avoid serious side effects, i.e., to provide a reasonable benefit to risk ratio, within the scope of sound medical judgment.

Active and other ingredients useful herein may be categorized or described herein by their cosmetic and/or therapeutic benefit or their postulated mode of action. However, it is to be understood that the active and other ingredients useful herein can in some instances provide more than one cosmetic and/or therapeutic benefit or operate via more than one mode of action. Therefore, classifications herein are made for the sake of convenience and are not intended to limit an ingredient to the particularly stated application or applications listed.

The compositions of the invention are useful for topical application and for providing an essentially immediate (i.e., acute) visual improvement in skin appearance following application of the composition to the skin. Without intending to be limited by theory, it is believed that this acute skin appearance improvement results at least in part from therapeutic coverage or masking of skin imperfections by the particulate material. The compositions provide the visual benefits without imparting an unacceptable skin appearance such as skin whitening.

More particularly, the compositions of the present invention are useful for regulating skin condition, including regulating visible and/or tactile discontinuities in skin, including but not limited to visible and/or tactile discontinuities in skin texture and/or color, more especially discontinuities associated with skin aging. Such discontinuities may be induced or caused by internal and/or external factors. Extrinsic factors include ultraviolet radiation (e.g., from sun exposure), environmental pollution, wind, heat, low humidity, harsh surfactants, abrasives, and the like. Intrinsic factors include chronological aging and other biochemical changes from within the skin.

Regulating skin condition includes prophylactically and/or therapeutically regulating skin condition. As used herein, prophylactically regulating skin condition includes delaying, minimizing and/or preventing visible and/or tactile discontinuities in skin. As used herein, therapeutically regulating skin condition includes ameliorating, e.g., diminishing, minimizing and/or effacing, such discontinuities. Regulating skin condition involves improving skin appearance and/or feel, e.g., providing a smoother, more even appearance and/or feel. As used herein, regulating skin condition includes regulating signs of aging. "Regulating signs of skin aging" includes prophylactically regulating and/or therapeutically regulating one or more of such signs (similarly, regulating a given sign of skin aging, e.g., lines, wrinkles or pores, includes prophylactically regulating and/or therapeutically regulating that sign).

"Signs of skin aging" include, but are not limited to, all outward visibly and tactilely perceptible manifestations as well as any other macro or micro effects due to skin aging. Such signs may be induced or caused by intrinsic factors or extrinsic factors, e.g., chronological aging and/or environmental damage. These signs may result from processes which include, but are not limited to, the development of textural discontinuities such as wrinkles, including both fine superficial wrinkles and coarse deep wrinkles, skin lines, crevices, bumps, large pores (e.g., associated with adnexal structures such as sweat gland ducts, sebaceous glands, or hair follicles), scaliness, flakiness and/or other forms of skin unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

It is to be understood that the present invention is not to be limited to regulation of the above mentioned "signs of skin aging" which arise due to mechanisms associated with skin aging, but is intended to include regulation of said signs irrespective of the mechanism of origin. As used herein, "regulating skin condition" is intended to include regulation of such signs irrespective of the mechanism of origin.

The present invention is especially useful for therapeutically regulating visible and/or tactile discontinuities in mammalian skin, including discontinuities in skin texture and color. For example, the apparent diameter of pores decreases, the apparent height of tissue immediately proximate to pore openings approaches that of the interadnexal skin, the skin tone/color becomes more uniform, and/or the length, depth, and/or other dimension of lines and/or wrinkles are decreased.

Particulate material

The compositions of the present invention comprise a safe and effective amount of a particulate material having a refractive index of at least about 2, more preferably at least about 2.5, e.g., from about 2 to about 3. The particulate material is dispersed in a dermatologically acceptable carrier.

Refractive index can be determined by conventional methods. For example, a method for determining the refractive index which is applicable to the present invention is described in J. A. Dean, Ed., Lange's Handbook of Chemistry, 14th Ed., McGraw Hill, New York, 1992, Section 9, Refractometry, incorporated herein by reference in its entirety.

The particulate material preferably comprises particles of inorganic material comprising $TiO_2$, $ZnO$, $ZrO_2$ and combinations thereof, more preferably $TiO_2$, $ZnO$ and combinations thereof (combinations are intended to include particles which comprise one or more of these materials, as well as mixtures of these particulate materials). The particulate material may be a composite, e.g., deposited on a core or mixed with other materials such as but not limited to silica, silicone, mica, nylon and polyacrylates, provided that the material has the aforementioned refractive index. The particulate preferably consists essentially of $TiO_2$, $ZnO$, $ZrO_2$ or a combination thereof, more preferably $TiO_2$, $ZnO$ or a combination thereof, most preferably, the particles consist essentially of $TiO_2$.

Pigmentary grade particulate material is preferred. Preferred particulate materials are those having a primary particle size of from about 100 nm to about 300 nm, more preferably greater than 100 nm to about 300 nm, even more preferably from about 150 nm to about 300 nm, most preferably from about 200 nm to about 250 nm (e.g., about 220 to about 240 nm), in the neat form (i.e., in the essentially pure, powder form prior to combination with any carrier). Preferred particulate materials have a primary particle size when dispersed in the composition of from about 100 nm to about 1000 nm (preferably greater than 100 nm), more preferably from about 100 nm to about 400 nm, even more preferably from about 200 nm to about 300 nm. Primary particle size can be determined using the ASTM Designation E20–85 "Standard Practice for Particle Size Analysis of Particulate Substances in the Range of 0.2 to 75 Micrometers by Optical Microscopy", ASTM Volume 14.02, 1993, incorporated herein by reference.

The particles may have a variety of shapes, including spherical, spheroidal, elliptical, lamellar, irregular, needle and rod-like, provided that the desired refractive index is provided. The particulate can be in a variety of physical forms, including rutile, anatase or a combination thereof.

The compositions of the present invention preferably comprise from about 0.1% to about 3% of the particulate material. Especially preferred are topical compositions containing from about 0.3% to about 2%, more preferably from about 0.5% to about 1%, of the particulate material.

The particulate material can be water-dispersible, oil-dispersible, or a combination thereof. Water- or oil- dispersibility may be inherent to the particle or may be imparted by coating the particles with material to impart a hydrophilic or hydrophobic surface property to the particles. For example, hydrophilic coatings may comprise an amino acid, aluminum oxide or aluminum silicate. Exemplary hydrophobic coatings may comprise organosilicone compounds or metal soaps such as aluminum stearate, aluminum laurate, and zinc stearate.

Inorganic particulate materials, e.g., comprising $TiO_2$, ZnO or $ZrO_2$ are commercially available from a number of sources. Nonlimiting examples of suitable particulate materials are available from Warner Jenkinson (C-9729, a hydrophobic, dimethicone treated, anatase form $TiO_2$); U.S. Cosmetics (TRONOX $TiO_2$ series, e.g., AT-T-CR837, a hydrophilic, rutile, amino acid treated $TiO_2$; AT-T-328, a hydrophilic, anatase, amino acid treated $TiO_2$; and SAT-T CR837, a rutile $TiO_2$); and Kobo (TRONOX $TiO_2$ series, e.g., ST490, a rutile, silane treated $TiO_2$). The particulate materials are available in essentially neat, powdered form or predispersed in various types of dispersants, including but not limited to isopropyl isostearate, isopropyl palmitate, methyl isostearate, Finsolv TN, cylcomethicone, and cyclomethicone and dimethicone copolyols.

The compositions may contain other inorganic or organic particulate materials, e.g., fillers or pigments, provided that they do not significantly reduce the benefits of the invention. For example, the total amount of all particulate material in the composition (including the above-described particulate having a refractive index of at least about 2 and any other particulate), by weight %, may be about 10 or less, about 5 or less, or about 3 or less. It is preferred that the particulates in the compositions of the invention consist essentially of the particulate material described in this section entitled "Particulate Material."

Carrier

The compositions of the present invention comprise a safe and effective amount of a dermatologically acceptable carrier within which the essential particulate material and optional other materials are incorporated to enable the particulate material and optional components to be delivered to the skin at an appropriate concentration. The carrier can thus act as a diluent, dispersant, solvent, or the like for the particulate material which ensures that it can be applied to and distributed evenly over the selected target at an appropriate concentration.

The carrier may contain one or more dermatologically acceptable solid, semi-solid or liquid fillers, diluents, solvents, extenders and the like. The carrier may be solid, semi-solid or liquid. Preferred carriers are substantially liquid. The carrier can itself be inert or it can possess dermatological benefits of its own. Concentrations of the carrier can vary with the carrier selected and the intended concentrations of the essential and optional components.

Suitable carriers include conventional or otherwise known carriers that are dermatologically acceptable. The carrier should also be physically and chemically compatible with the essential components described herein, and should not unduly impair stability, efficacy or other use benefits associated with the compositions of the present invention. Preferred components of the compositions of this invention should be capable of being comingled in a manner such that there is no interaction which would substantially reduce the efficacy of the composition under ordinary use situations.

The type of carrier utilized in the present invention depends on the type of product form desired for the composition. The topical compositions useful in the subject invention may be made into a wide variety of product forms such as are known in the art. These include, but are not limited to, lotions, creams, gels, sticks, sprays, ointments, pastes, mousses and cosmetics (e.g., solid, semi-solid, or liquid make-up, including foundations, eye-makeup, pigmented or non-pigmented lip treatments, e.g., lipsticks, and the like). These product forms may comprise several types of carriers including, but not limited to, solutions, aerosols, emulsions, gels, solids, and liposomes.

Preferred carriers contain a dermatologically acceptable, hydrophilic diluent. As used herein, "diluent" includes materials in which the particulate material can be dispersed, dissolved, or otherwise incorporated. Nonlimiting examples of hydrophilic diluents are water, organic hydrophilic diluents such as lower monovalent alcohols (e.g., $C_1$–$C_4$) and low molecular weight glycols and polyols, including propylene glycol, polyethylene glycol (e.g., Molecular Weight 200–600 g/mole), polypropylene glycol (e.g., Molecular Weight 425–2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof. Water is a preferred diluent. The composition preferably comprises from about 60% to about 99.99% of the hydrophilic diluent.

Solutions according to the subject invention typically include a dermatologically acceptable hydrophilic diluent. Solutions useful in the subject invention preferably contain from about 60% to about 99.99% of the hydrophilic diluent.

Aerosols according to the subject invention can be formed by adding a propellant to a solution such as described above. Exemplary propellants include chloro-fluorinated lower molecular weight hydrocarbons. Additional propellants that are useful herein are described in Sagarin, Cosmetics Science and Technology 2nd Edition, Vol. 2, pp. 443–465 (1972), incorporated herein by reference. Aerosols are typically applied to the skin as a spray-on product.

Preferred carriers comprise an emulsion comprising a hydrophilic phase comprising a hydrophilic component, e.g., water or other hydrophilic diluent, and a hydrophobic phase comprising a hydrophobic component, e.g., a lipid, oil or oily material. As well known to one skilled in the art, the hydrophilic phase will be dispersed in the hydrophobic phase, or vice versa, to form respectively hydrophilic or hydrophobic dispersed and continuous phases, depending on the composition ingredients. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The emulsion may be or comprise (e.g., in a triple or other multi-phase emulsion) an oil-in-water emulsion or a water-in-oil emulsion such as a water-in-silicone emulsion. Oil-in-water emulsions typically comprise from about 1% to about 50% (preferably about 1% to about 30%) of the dispersed hydrophobic phase and from about 1% to about 98% (preferably from about 40% to about 90%) of the continuous hydrophilic phase; water-in-oil emulsions typically comprise from about 1% to about 98% (preferably from about 40% to about 90%) of the dispersed hydrophilic phase and from about 1% to about 50% (preferably about 1% to about 30%) of the continuous hydrophobic phase. The emulsion may also comprise a gel network, such as described in G. M. Eccleston, Application of Emulsion Stability Theories to Mobile and Semisolid O/W Emulsions, Cosmetics & Toiletries, Vol. 101, November 1996, pp. 73–92, incorporated herein by reference. Preferred emulsions are further described below.

The topical compositions of the subject invention, including but not limited to lotions and creams, may comprise a dermatologically acceptable emollient. Such compositions preferably contain from about 2% to about 50% of the emollient. Emollients tend to lubricate the skin, increase the smoothness and suppleness of the skin, prevent or relieve dryness of the skin, and/or protect the skin. Emollients are typically water-immiscible, oily or waxy materials. A wide variety of suitable emollients are known and may be used herein. Sagarin, *Cosmetics, Science and Technology,* 2nd Edition, Vol. 1, pp. 32–43 (1972), incorporated herein by reference, contains numerous examples of materials suitable as an emollient.

Lotions and creams according to the present invention generally comprise a solution carrier system and one or more emollients. Lotions typically comprise from about 1% to about 20%, preferably from about 5% to about 10%, of emollient; from about 50% to about 90%, preferably from about 60% to about 80%, water. A cream typically comprises from about 5% to about 50%, preferably from about 10% to about 20%, of emollient; and from about 45% to about 85%, preferably from about 50% to about 75%/, water.

Ointments of the present invention may comprise a simple carrier base of animal or vegetable oils or semi-solid hydrocarbons (oleaginous); absorption ointment bases which absorb water to form emulsions; or water soluble carriers, e.g., a water soluble solution carrier. Ointments may further comprise a thickening agent, such as described in Sagarin, *Cosmetics, Science and Technology,* 2nd Edition, Vol. 1, pp. 72–73 (1972), incorporated herein by reference, and/or an emollient. For example, an ointment may comprise from about 2% to about 10% of an emollient; and from about 0.1% to about 2% of a thickening agent.

Compositions of this invention useful for cleansing ("cleansers") are formulated with a suitable carrier, e.g., as described above, and preferably contain one or more dermatologically acceptable surfactants in an amount which is safe and effective for cleansing. Preferred compositions contain from about 1% to about 90%, more preferably from about 5% to about 10%, of a dermatologically acceptable surfactant. The surfactant is suitably selected from anionic, cationic, nonionic, zwitterionic, amphoteric and ampholytic surfactants, as well as mixtures of these surfactants. Such surfactants are well known to those skilled in the detergency art. Nonlimiting examples of possible surfactants include isoceteth-20, sodium methyl cocoyl taurate, sodium methyl oleoyl taurate, sodium lauryl sulfate, and betaines such as described herein. See U.S. Pat. No. 4,800,197, to Kowcz et al., issued Jan. 24, 1989, which is incorporated herein by reference in its entirety, for exemplary surfactants useful herein. Examples of a broad variety of additional surfactants useful herein are described in *McCutcheon's Detergents and Emulsifiers,* North American Edition (1986), published by Allured Publishing Corporation, which is incorporated herein by reference in its entirety. The cleansing compositions can optionally contain, at their art-established levels, other materials which are conventionally used in cleansing compositions.

The physical form of the cleansing compositions is not critical. The compositions can be, for example, formulated as toilet bars, liquids, shampoos, bath gels, hair conditioners, hair tonics, pastes, or mousses. Toilet bars are most preferred since this is the form of cleansing agent most commonly used to wash the skin. Preferred rinse-off cleansing compositions, such as shampoos, include a delivery system adequate to deposit sufficient levels of actives on the skin and scalp. A preferred delivery system involves the use of insoluble complexes. For a more complete disclosure of such delivery systems, see U.S. Pat. No. 4,835,148, Barford et al., issued May 30, 1989, incorporated herein by reference in its entirety.

As used herein, the term "foundation" refers to a liquid, semi-liquid, semi-solid, or solid skin cosmetic which includes, but is not limited to lotions, creams, gels, pastes, cakes, and the like. Typically the foundation is used over a large area of the skin, such as over the face, to provide a particular look. Foundations are typically used to provide an adherent base for color cosmetics such as rouge, blusher, powder and the like, and tend to hide skin imperfections and impart a smooth, even appearance to the skin. Foundations of the present invention include a dermatologically acceptable carrier for the essential particulate material and may include conventional ingredients such as oils, colorants, pigments, emollients, fragrances, waxes, stabilizers, and the like. Exemplary carriers and such other ingredients which are suitable for use herein are described, for example, in copending patent application Ser. No. 08/430,961, filed on Apr. 28, 1995 in the names of Marcia L. Canter, Brain D. Barford, and Brian D. Hofrichter, incorporated herein by reference.

The compositions of the present invention are preferably formulated to have a pH of 10.5 or below. The pH values of these compositions preferably range from about 2 to about 10.5, more preferably from about 3 to about 8, even more preferably from about 5 to about 8.

Preferred compositions of this invention

Preferred topical compositions of the present invention comprise an emulsion. Emulsions of the present invention may contain one or more of the following:

a) Hydrophobic component

Emulsions according to the present invention contain a hydrophobic phase comprising a lipid, oil, oily or other hydrophobic component. The compositions of the present invention preferably comprise from about 1% to about 50%, preferably from about 1% to about 30%, and more preferably from about 1% to about 10% by weight of the composition of a hydrophobic component. The hydrophobic component may be derived from animals, plants, or petroleum and may be natural or synthetic (i.e., man-made). Preferred hydrophobic components are substantially water-insoluble, more preferably essentially water-insoluble. Preferred hydrophobic components are those having a melting point of about 25° C. or less under about one atmosphere of pressure, and are suitable for conditioning the skin or hair.

Nonlimiting examples of suitable hydrophobic components include those selected from the group consisting of:

(1) Mineral oil, which is also known as petrolatum liquid, is a mixture of liquid hydrocarbons obtained from petroleum. See The Merck Index, Tenth Edition, Entry 7048, p. 1033 (1983) and International Cosmetic Ingredient Dictionary, Fifth Edition, vol. 1, p.415–417 (1993), which are incorporated by reference herein in their entirety.

(2) Petrolatum which is also known as petroleum jelly, is a colloidal system of nonstraight-chain solid hydrocarbons and high-boiling liquid hydrocarbons, in which most of the liquid hydrocarbons are held inside the micelles. See The Merck Index, Tenth Edition, Entry 7047, p. 1033 (1983); Schindler, *Drug. Cosmet. Ind.*, 89, 36–37, 76, 78–80, 82 (1961); and International Cosmetic Ingredient Dictionary, Fifth Edition, vol. 1, p. 537 (1993), which are incorporated by reference herein in their entirety.

(3) Straight and branched chain hydrocarbons having from about 7 to about 40 carbon atoms. Nonlimiting examples of these hydrocarbon materials include dodecane, isododecane, squalane, cholesterol, hydrogenated polyisobutylene, docosane (i.e. a $C_{22}$ hydrocarbon), hexadecane, isohexadecane (a commercially available hydrocarbon sold as Permethyl® 101A by Presperse, South Plainfield, N.J.). Also useful are the C7–C40 isoparaffins, which are C7–C40 branched hydrocarbons.

(4) C1–C30 alcohol esters of C1–C30 carboxylic acids and of C2–C30 dicarboxylic acids including straight and branched chain materials as well as aromatic derivatives (as used herein in reference to the hydrophobic component, mono- and poly-carboxylic acids include straight chain, branched chain and aryl carboxylic acids). Nonlimiting examples include diisopropyl sebacate, diisopropyl adipate, isopropyl myristate, isopropyl palmitate, methyl palmitate, myristyl propionate, 2-ethylhexyl palmitate, isodecyl neopentanoate, di-2-ethylhexyl maleate, cetyl palmitate, myristyl myristate, stearyl stearate, isopropyl stearate, methyl stearate, cetyl stearate, behenyl behenrate, dioctyl maleate, dioctyl sebacate, diisopropyl adipate, cetyl octanoate, diisopropyl dilinoleate.

(5) mono-. di- and tri- glycerides of C1–C30 carboxylic acids, e.g., caprilic/capric triglyceride, PEG-6 caprylic/capric triglyceride, PEG-8 caprylic/capric triglyceride.

(6) alkylene glycol esters of C1–C30 carboxylic acids, e.g., ethylene glycol mono -and di- esters, and propylene glycol mono- and di- esters of C1–C30 carboxylic acids e.g., ethylene glycol distearate.

(7) propoxylated and ethoxylated derivatives of the foregoing materials.

(8) C1–C30 mono- and poly- esters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7–8, and in which the fatty acid moieties are C18 mono- and/or di-unsaturated and behenic, in a molar ratio of unsaturates-:behenic of 1:7 to 3:5. A particularly preferred solid sugar polyester is the octaester of sucrose in which there are about 7 behenic fatty acid moieties and about 1 oleic acid moiety in the molecule. Other materials include cottonseed oil or soybean oil fatty acid esters of sucrose. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

9) Organopolysiloxane oils. The organopolysiloxane oil may be volatile, nonvolatile, or a mixture of volatile and non-volatile silicones. The term "nonvolatile" as sed in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Nonvolatile polysiloxanes are preferred. Nonlimiting examples of suitable silicones are disclosed in U.S. Pat. No. 5,069,897, to Orr, issued Dec. 3, 1991, which is incorporated by reference herein in its entirety. Examples of suitable organopolysiloxane oils include polyalkylsiloxanes, cyclic polyalkylsiloxanes, and polyalkylarylsiloxanes.

Polyalkylsiloxanes useful in the composition herein include polyalkylsiloxanes with viscosities of from about 0.5 to about 1,000,000 centistokes at 25° C. Such polyalkylsiloxanes can be represented by the general chemical formula $R_3SiO[R_2SiO]_xSiR_3$ wherein R is an alkyl group having from one to about 30 carbon atoms (preferably R is methyl or ethyl, more preferably methyl; also mixed alkyl groups can be used in the same molecule), and x is an integer from 0 to about 10,000, chosen to achieve the desired molecular weight which can range to over about 10,000,000. Commercially available polyalkylsiloxanes include the polydimethylsiloxanes, which are also known as dimethicones, examples of which include the Vicasil® series sold by General Electric Company and the Dow Corning® 200 series sold by Dow Corning Corporation. Specific examples of suitable polydimethylsiloxanes include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Suitable dimethicones include those represented by the chemical formula $(CH_3)_3SiO[(CH_3)_2SiO]_x[CH_3RSiO]_ySi(CH_3)_3$ wherein R is straight or branched chain alkyl having from two to about 30 carbon atoms and x and y are each integers of 1 or greater selected to achieve the desired molecular weight which can range to over about 10,000,000. Examples of these alkyl-substituted dimethicones include cetyl dimethicone and lauryl dimethicone.

Cyclic polyalkylsiloxanes suitable for use in the composition include those represented by the chemical formula $[SiR_2\text{-}O]_n$ wherein R is an alkyl group (preferably R is methyl or ethyl, more preferably methyl) and n is an integer from about 3 to about 8, more preferably n is an integer from about 3 to about 7, and most preferably n is an integer from about 4 to about 6. When R is methyl, these materials are typically referred to as cyclomethicones. Commercially available cyclomethicones include Dow Corning® 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains the cyclomethicone pentamer (i.e. n=5), Dow Corning® 245 fluid having a viscosity of 4.2 centistokes and a boiling point of 205° C., which primarily contains a mire of the cyclomethicone tetramer and pentamer (i.e. n=4 and 5), and Dow Corning® 345 fluid having a viscosity of 4.5 centistokes and a boiling point of 217°, which primarily contains a mixture of the cyclomethicone tetramer, pentamer, and hexamer (i.e. n=4, 5, and 6).

Also useful are materials such as trimethylsiloxysilicate, which is a polymeric material corresponding to the general chemical formula $[(CH_2)_3SiO_{1/2}]_x[SiO_2]y$, wherein x is an integer from about 1 to about 500 and y is an integer from about 1 to about 500. A commercially available trimethylsiloxysilicate is sold as a mixture with dimethicone as Dow Corning® 593 fluid.

Dimethiconols are also suitable for use in the composition. These compounds can be represented by the chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer from 0 to about 500, chosen to achieve the desired molecular weight. Commercially available dimethiconols are typically sold as mixtures with dimethicone or cyclomethicone (e.g. Dow Corning® 1401, 1402, and 1403 fluids).

Polyalkylaryl siloxanes are also suitable for use in the composition. Polymethylphenyl siloxanes having viscosities from about 15 to about 65 centistokes at 25° C. are especially useful.

Preferred for use herein are organopolysiloxanes selected from the group consisting of polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones.

(10) Vegetable oils and hydrogenated vegetable oils. Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, and mixtures thereof.

(11) animal fats and oils, e.g., lanolin and derivatives thereof, cod liver oil.

(12) Also useful are C4–C20 alkyl ethers of polypropylene glycols, C1–C20 carboxylic acid esters of polypropylene glycols, and di-C8-C30 alkyl ethers. Nonlimiting examples of these materials include PPG-14 butyl ether, PPG-15 stearyl ether, dioctyl ether, dodecyl octyl ether, and mixtures thereof.

b) Hydrophilic component

Emulsions of the present invention also comprise a hydrophilic component, e.g., water or other hydrophilic diluent. The hydrophilic phase can thus comprise water, or a combination of water and one or more water soluble or dispersible ingredients. Hydrophilic components comprising water are preferred.

(c) Other components

Emulsions and other topical compositions of the present invention may comprise a variety of other ingredients such as disclosed herein. As will be understood by the skilled artisan, a given component will distribute primarily into either a hydrophilic phase or hydrophobic phase, depending on the hydrophilicity of the component in the composition. Emulsions of the present invention preferably include one or more compounds selected from emulsifiers, surfactants, structuring agents, and thickeners. Compositions containing these ingredients tend to have the preferred apparent viscosities described herein.

(1) Emulsifiers/Surfactants

The emulsion may contain an emulsifier and/or surfactant, generally to help disperse and suspend the discontinuous phase within the continuous phase. A wide variety of such agents can be employed. Known or conventional emulsifiers/surfactants can be used in the composition, provided that the selected agent is chemically and physically compatible with essential components of the composition, and provides the desired dispersion characteristics. Suitable agents include non-silicone-containing emulsifiers/surfactants, silicone emulsifiers/surfactants, and mixtures thereof.

In a preferred embodiment, the composition comprises a hydrophilic emulsifier or surfactant. The compositions of the present invention preferably comprise from about 0.05% to about 5%, more preferably from about 0.05% to about 1% of at least one hydrophilic surfactant. Without intending to be limited by theory, it is believed that the hydrophilic surfactant assists in dispersing hydrophobic materials, e.g., hydrophobic structuring agents, in the hydrophilic phase. The surfactant, at a minimum, must be hydrophilic enough to disperse in the hydrophilic phase. Preferred surfactants are those having an HLB of at least about 8. The exact surfactant chosen will depend upon the pH of the composition and the other components present.

Preferred hydrophilic surfactants are selected from nonionic surfactants. Among the nonionic surfactants that are useful herein are those that can be broadly defined as condensation products of long chain alcohols, e.g. C8–30 alcohols, with sugar or starch polymers, i.e., glycosides. These compounds can be represented by the formula $(S)_n$-O-R wherein S is a sugar moiety such as glucose, fructose, mannose, and galactose; n is an integer of from about 1 to about 1000, and R is a C8–30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8–20 alkyl group, and n is an integer of from about 1 to about 9. Commercially available examples of these surfactants include decyl polyglucoside (available as APG 325 CS from Henkel) and lauryl polyglucoside (available as APG 600 CS and 625 CS from Henkel).

Other useful nonionic surfactants include the condensation products of alkylene oxides with fatty acids (i.e. alkylene oxide esters of fatty acids). These materials have the general formula RCO(X)$_n$OH wherein R is a C10–30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 6 to about 200. Other nonionic surfactants are the condensation products of alkylene oxides with 2 moles of fatty acids (i.e. alkylene oxide diesters of fatty acids). These materials have the general formula RCO(X)$_n$OOCR wherein R is a C10–30 allyl group, X is —OCH$_2$CH$_2$—(i.e. derived from ethylene glycol or oxide) or —OCH$_2$CHCH$_3$—(i.e. derived from propylene glycol or oxide), and n is an integer from about 6 to about 100. Other nonionic surfactants are the condensation products of alkylene oxides with fatty alcohols (i.e. alkylene oxide ethers of fatty alcohols). These materials have the general formula R(X)$_n$OR' wherein R is a C10–30 alkyl group, X is —OCH$_2$CH$_2$—(i.e. derived from ethylene glycol or oxide) or —OCH$_2$CHCH$_3$— (i.e. derived from propylene glycol or oxide), and n is an integer from about 6 to about 100 and R' is H or a C10–30 alkyl group. Still other nonionic surfactants are the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. These materials have the general formula RCO(X)$_n$OR' wherein R and R' are C10–30 alkyl groups, X is —OCH$_2$CH$_2$ (i.e. derived from ethylene glycol or oxide) or —OCH$_2$CHCH$_3$— (derived from propylene glycol or oxide), and n is an integer from about 6 to about 100.

Nonlimiting examples of these alkylene oxide derived nonionic surfactants include ceteth-6, ceteth-10, ceteth-12, ceteareth-6, ceteareth-10, ceteareth-12, steareth-6, steareth-10, steareth-12, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants corresponding to the structural formula:

wherein: R$^1$ is H, C$_1$–C$_4$ alkyl, 2-hydroxyethyl, 2-hydroxypropyl, preferably C$_1$–C$_4$ 10 alkyl, more preferably methyl or ethyl, most preferably methyl; R is C$_5$–C$_{31}$ alkyl or alkenyl, preferably C$_7$–C$_{19}$ alkyl or alkenyl, more preferably C$_9$–C$_{17}$ alkyl or alkenyl, most preferably C$_{11}$–C$_{15}$ alkyl or alkenyl; and Z is a polhydroxyhydrocarbyl moiety having a linear hydrocarbyl chain with a least 3 hydroxyls directly connected to the echain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the R$^2$CO— moiety is derived from coconut oil fatty acids). Processes for making compositions containing polyhydroxy fatty acid amides are disclosed, for example, in G.B. Patent Specification 809,060, published Feb. 18, 1959, by Thomas Hedley & Co., Ltd.; U.S. Pat. No. 2,965,576, to E. R Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934; which are incorporated herein by reference in their entirety.

Preferred among the nonionic surfactants are those selected from the group consisting of steareth-21, ceteareth-20, ceteareth-12, sucrose cocoate, steareth-100, PEG-100 stearate, and mixtures thereof.

Other nonionic surfactants suitable for use herein include sugar esters and polyesters, alkoxylated sugar esters and polyesters, C1–C30 fatty acid esters of C1–C30 fatty alcohols, alkoxylated derivatives of C1–C30 fatty acid esters of C1–C30 fatty alcohols, alkoxylated ethers of C1–C30 fatty alcohols, polyglyceryl esters of C1–C30 fatty acids, C1–C30 esters of polyols, C1–C30 ethers of polyols, alkyl phosphates, polyoxyalkylene fatty ether phosphates, fatty acid amides, acyl lactylates, and mixtures thereof. Nonlimiting examples of these non-silicon-containing emulsifiers include: polyethylene glycol 20 sorbitan monolaurate Polysorbate 20), polyethylene glycol 5 soya sterol, Steareth-20, Ceteareth-20, PPG-2 methyl glucose ether distearate, Ceteth- 10, Polysorbate 80, cetyl phosphate, potassium cetyl phosphate, diethanolamine cetyl phosphate, Polysorbate 60, glyceryl stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, PEG-100 stearate, and mixtures thereof.

Another emulsifier useful herein are fatty acid ester blends based on a mixture of sorbitan or sorbitol fatty acid ester and sucrose fatty acid ester, the fatty acid in each instance being preferably C$_8$–C$_{24}$, more preferably C$_{10}$–C$_{20}$. The preferred fatty acid ester emulsifier is a blend of sorbitan or sorbitol C$_{16}$–C$_{20}$ fatty acid ester with sucrose C$_{10}$–C$_{16}$ fatty acid ester, especially sorbitan stearate and sucrose cocoate. This is commercially available from ICI under the trade name Arlatone 2121.

The hydrophilic surfactants useful herein can alternatively or additionally include any of a wide variety of cationic, anionic, zwitterionic, and amphoteric surfactants such as are known in the art. See, e.g., McCutcheon's, *Detergents and Emulsifiers,* North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety.

Exemplary cationic surfactants useful herein include those disclosed in U.S. Pat. No. 5,151,209, to McCall et al., issued Sep. 29, 1992; U.S. Pat. No. 5,151,210, to Steuri et al., issued Sep. 29, 1992; U.S. Pat. No. 5,120,532, to Wells et al., issued Jun. 9, 1992; U.S. Pat. No. 4,387,090, to Bolich, issued Jun. 7, 1983;; U.S. Patent 3,155,591, Hilfer, issued Nov. 3, 1964; U.S. Pat. No. 3,929,678, to Laughlin et al., issued Dec. 30, 1975; U.S. Pat. No. 3,959,461, to Bailey et al., issued May 25, 1976; *McCutcheon's, Detergents & Emulsifiers,* (North American edition 1979) M.C. Publishing Co.; and Schwartz, et al., *Surface Active Agents Their Chemistry and Technology,* New York: Interscience Publishers, 1949; all of these documents being incorporated herein by reference in their entirety. The cationic surfactants useful herein include cationic ammonium salts such as quaternary ammonium salts, and amino-amides.

A wide variety of anionic surfactants are also useful herein. See, e.g., U.S. Pat. No. 3,929,678, to Laughlin et al., issued Dec. 30, 1975, which is incorporated herein by reference in its entirety. Nonlimiting examples of anionic surfactants include the alkoyl isethionates (e.g., $C_{12}$–$C_{30}$), allyl and alkyl ether sulfates and salts thereof, alkyl and allyl ether phosphates and salts thereof, alkyl methyl taurates (e.g., $C_{12}$–$C_{30}$), and soaps (e.g., alkali metal salts, e.g., sodium or potassium salts) of fatty acids.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$–$C_{18}$) and one contains an anionic water solubilizing group, e.g., carboxy, sulfonate, sulfate, phosphate, or phosphonate. Examples are alkyl imino acetates, and iminodialkanoates and aminoalkanoates, imidazolinium and ammonium derivatives. Other suitable amphoteric and zwitterionic surfactants are those selected from the group consisting of betaines, sultaines, hydroxysultaines, alkyl sarcosinates (e.g., $C_{12}$–$C_{30}$), and alkanoyl sarcosinates.

Preferred emulsions of the present invention include a silicone containing emulsifier or surfactant. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include allyl-modified dimethicone copolyols, i.e., compounds which contain C2-C30 pendant side chains. Still other useful dimethicone copolyols include materials having various cationic, anionic, amphoteric, and zwitterionic pendant moieties.

The dimethicone copolyol emulsifiers useful herein can be described by the following general structure:

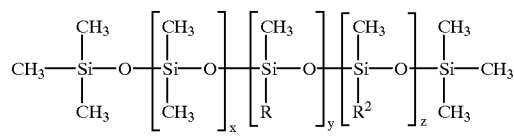

wherein R is C1–C30 straight, branched, or cyclic allyl and $R^2$ is selected from the group consisting of

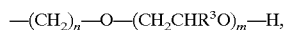

and

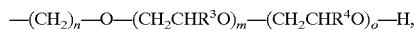

wherein n is an integer from 3 to about 10; $R^3$ and $R^4$ are selected from the group consisting of H and C1–C6 straight or branched chain alkyl such that $R^3$ and $R^4$ are not simultaneously the same; and m, o, x, and y are selected such that the molecule has an overall molecular weight from about 200 to about 10,000,000, with m, o, x, and y being independently selected from integers of zero or greater such that m and o are not both simultaneously zero, and z being independently selected from integers of 1 or greater. It is recognized that positional isomers of these copolyols can be achieved. The chemical representations depicted above for the $R^2$ moieties containing the $R^3$ and $R^4$ groups are not meant to be limiting but are shown as such for convenience.

Also useful herein, although not strictly classified as dimethicone copolyols, are silicone surfactants as depicted in the structures in the previous paragraph wherein $R^2$ is:

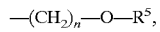

wherein $R^5$ is a cationic, anionic, amphoteric, or zwitterionic moiety.

Nonlimiting examples of dimethicone copolyols and other silicone surfactants useful as emulsifiers herein include polydimethylsiloxane polyether copolymers with pendant polyethylene oxide sidechains, polydimethylsiloxane polyether copolymers with pendant polypropylene oxide sidechains, polydimethylsiloxane polyether copolymers with pendant mixed polyethylene oxide and polypropylene oxide sidechains, polydimethylsiloxane polyether copolymers with pendant mixed poly(ethylene)(propylene)oxide sidechains, polydimethylsiloxane polyether copolymers with pendant organobetaine sidechains, polydimethylsiloxane polyether copolymers with pendant carboxylate sidechains, polydimethylsiloxane polyether copolymers with pendant quaternary ammonium sidechains; and also further modifications of the preceding copolymers containing pendant C2–C30 straight, branched, or cyclic alkyl moieties. Examples of commercially available dimethicone copolyols useful herein sold by Dow Corning Corporation are Dow Corning® 190, 193, Q2-5220, 2501 Wax, 2-5324 fluid, and 3225C (this later material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate (and) cetyl dimethicone and is sold under the tradename ABIL® WS-08 (also available from Goldschmidt). Other nonimiting examples of dimethicone copolyols also include lauryl dimethicone copolyol, dimethicone copolyol acetate, dimethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate. See *International Cosmetic Ingredient Dictionary*, Fifth Edition, 1993, which is incorporated by reference herein in its entirety.

Dimethicone copolyol emulsifiers useful herein are described, for example, in U.S. Pat. No. 4,960,764, to Figueroa, Jr. et al., issued Oct. 2, 1990; European Pat. No. EP 330,369, to SaNogueira, published Aug. 30, 1989; G. H. Dahms, et al., "New Formulation Possibilities Offered by Silicone Copolyols," *Cosmetics & Toiletries,* vol. 110, pp. 91–100, March 1995; M. E. Carlotti et al., "Optimization of W/O-S Emulsions And Study Of The Quantitative Relationships Between Ester Structure And Emulsion Properties," *J. Dispersion Science And Technology,* 13(3), 315–336 (1992); P. Hameyer, "Comparative Technological Investigations of Organic and Organosilicone Emulsifiers in Cosmetic Water-in-Oil Emulsion Preparations," HAPPI 28(4), pp. 88–128 (1991); J. Smid-Korbar et al., "Efficiency and usability of silicone surfactants in emulsions," *Provisional Communication, International Journal of Cosmetic Science,* 12, 135–139 (1990); and D. G. Krzysik et al., "A New Silicone Emulsifier For Water-in-Oil Systems," *Drug and Cosmetic Industry* vol. 146(4) pp. 28–81 (April 1990); incorporated by reference herein in their entirety.

(2) Structuring Agent

The compositions hereof, and especially the emulsions hereof, may contain a structuring agent. Structuring agents are particularly preferred in the oil-in-water emulsions of the present invention. Without being limited by theory, it is believed that the structuring agent assists in providing rheological characteristics to the composition which contribute to the stability of the composition. For example, the structuring agent tends to assist in the formation of the liquid crystalline gel network structures. The structuring agent may also function as an emulsifier or surfactant. Preferred compositions of this invention comprise from about 1% to about 20%, more preferably from about 1% to about 10%, most preferably from about 2% to about 9%, of one or more structuring agents.

Preferred structuring agents are those having an HLB of from about 1 to about 8 and having a melting point of at least about 45° C. Suitable structuring agents are those selected from the group consisting of saturated $C_{14}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, $C_{14}$ to $C_{30}$ hydroxylated and nonhydroxylated saturated fatty acids, $C_{14}$ to $C_{30}$ saturated ethoxylated fatty acids, amines and alcohols containing from about 1 to about 5 moles of ethylene oxide diols, $C_{14}$ to $C_{30}$ saturated glyceryl mono esters with a monoglyceride content of at least 40%, $C_{14}$ to $C_{30}$ saturated polyglycerol esters having from about 1 to about 3 alkyl group and from about 2 to about 3 saturated glycerol units, $C_{14}$ to $C_{30}$ glyceryl mono ethers, $C_{14}$ to $C_{30}$ sorbitan mono/diesters, $C_{14}$ to $C_{30}$ saturated ethoxylated sorbitan mono/diesters with about 1 to about 5 moles of ethylene oxide, $C_{14}$ to $C_{30}$ saturated methyl glucoside esters, $C_{14}$ to $C_{30}$ saturated sucrose mono/diesters, $C_{14}$ to $C_{30}$ saturated ethoxylated methyl glucoside esters with about 1 to about 5 moles of ethylene oxide, $C_{14}$ to $C_{30}$ saturated polyglucosides having an average of between 1 to 2 glucose units and mixtures thereof, having a melting point of at least about 45° C.

The preferred structuring agents of the present invention are selected from the group consisting of stearic acid, palmitic acid, stearyl alcohol, cetyl alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More preferred structuring agents of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred structuring agents are selected from the group consisting of stearic acid, palmitic acid, stearyl alcohol, cetyl alcohol, behenyl alcohol, steareth-2, and mixtures thereof.

(3) Thickening Agent (including thickeners and gelling agents)

The compositions of the present invention can also comprise a thickening agent, preferably from about 0.1% to about 5%, more preferably from about 0.1% to about 3%, and most preferably from about 0.25% to about 2%, of a thickening agent.

Nonlimiting classes of thickening agents include those selected from the group consisting of:

(i) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. The preferred carboxylic acid polymers are of two general types. The first type of polymer is a crosslinked homopolymer of an acrylic acid monomer or derivative thereof (e.g., wherein the acrylic acid has substituents on the two and three carbon positions independently selected from the group consisting of $C_{1-4}$ alkyl, —CN, —COOH, and mixtures thereof). The second type of polymer is a crosslinked copolymer having a first monomer selected from the group consisting of an acrylic acid monomer or derivative thereof (as just described in the previous sentence), a short chain alcohol (i.e., a $C_{1-4}$) acrylate ester monomer or derivative thereof (e.g., wherein the acrylic acid portion of the ester has substituents on the two and three carbon positions independently selected from the group consisting of $C_{1-4}$ alkyl, —CN, —COOH and mixtures thereof), and mixtures thereof, and a second monomer which is a long chain alcohol (i.e. $C_{8-40}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof). Combinations of these two types of polymers are also useful herein.

In the first type of crosslinked homopolymers, the monomers are preferably selected from the group consisting of acrylic acid, methacrylic acid, ethacrylic acid, and mixtures thereof, with acrylic acid being most preferred. In the second type of crosslinked copolymers the acrylic acid monomer or derivative thereof is preferably selected from the group consisting of acrylic acid, methacrylic acid, ethacrylic acid, and mixtures thereof, with acrylic acid, methacrylic acid, and mixtures thereof being most preferred. The short chain alcohol acrylate ester monomer or derivative thereof is preferably selected from the group consisting of $C_{1-4}$ alcohol acrylate esters, $C_{1-4}$ alcohol methacrylate esters, $C_{1-4}$ alcohol ethacrylate esters, and mixtures thereof, with the $C_{1-4}$ alcohol acrylate esters, $C_{1-4}$ alcohol methacrylate esters, and mixtures thereof, being most preferred. The long chain alcohol acrylate ester monomer is selected from $C_{8-40}$ alkyl acrylate esters, with $C_{10-30}$ alkyl acrylate esters being preferred.

The crosslinking agent in both of these types of polymers is a polyalkenyl polyether of a polyhydric alcohol containing more than one alkenyl ether group per molecule, wherein the parent polyhydric alcohol contains at least 3 carbon atoms and at least 3 hydroxyl groups. Preferred crosslinkers are those selected from the group consisting of allyl ethers of sucrose and allyl ethers of pentaerythritol, and mixtures thereof. These polymers useful in the present invention are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; which are both incorporated by reference herein in their entirety. See also, *CTFA International Cosmetic Ingredient Dictionary,* fourth edition, 1991, pp. 12 and 80; which are also incorporated herein by reference in their entirety.

Examples of commercially available homopolymers of the first type useful herein include the carbomers, which are homopolymers of acrylic acid crosslinked with allyl ethers of sucrose or pentaerythritol. The carbomers are available as the Carbopol® 900 series from B. F. Goodrich (e.g., Carbopol® 954). Examples of commercially available copolymers of the second type useful herein include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytritol. These copolymers are known as acrylates/CIO-30 alkyl acrylate crosspolymers and are commercially available as Carbopol® 1342, Carbopol® 1382Pemulen TR-1, and Pemulen TR-2, from B. F. Goodrich. In other words, examples of carboxylic acid polymer thickeners useful herein are those selected from the group consisting of carbomers, acrylates/C10–C30 alkyl acrylate crosspolymers, and mixtures thereof.

(ii) Crosslinked Polyacrylate Polymers

The crosslinked polyacrylate polymers useful as thickeners or gelling agents include both cationic and nonionic polymers, with the cationics being generally preferred. Examples of useful crosslinked nonionic polyacrylate polymers and crosslinked cationic polyacrylate polymers are those described in U.S. Pat. No. 5,100,660, to Hawe et al., issued Mar. 31, 1992; U.S. Pat. No. 4,849,484, to Heard, issued Jul. 18, 1989; U.S. Pat. No. 4,835,206, to Farrar et al., issued May 30, 1989; U.S. Pat. No. 4,628,078 to Glover et al. issued Dec. 9, 1986; U.S. Pat. No. 4,599,379 to Flesher et al. issued Jul. 8, 1986; and EP 228,868, to Farrar et al., published Jul. 15, 1987; all of which are incorporated by reference herein in their entirety.

The crosslinked polyacrylate polymers are high molecular weight materials that can be characterized by the general formula: $(A)_l(B)_m(C)_n$ and comprise the monomer units $(A)_l$, $(B)_m$, and $(C)_n$, wherein (A) is a dialkylaminoalkyl acrylate monomer or its quaternary ammonium or acid addition salt, (13) is a dialkylaminoalkyl methacrylate monomer or its quaternary ammonium or acid addition salt, (C) is a monomer that is polymerizable with (A) or (B), for example a monomer having a carbon-carbon double bond or other such polymerizable functional group, I is an integer of 0 or greater, m is an integer of 0 or greater, n is an integer of 0 or greater, but where either l or m, or both, must be 1 or greater.

The (C) monomer can be selected from any of the commonly used monomers. Nonlimiting examples of these monomers include ethylene, propylene, butylene, isobutylene, eicosene, maleic anhydride, acrylamide, methacrylamide, maleic acid, acrolein, cyclohexene, ethyl vinyl ether, and methyl vinyl ether. In the cationic polymers of the present invention, (C) is preferably acrylamide. The alkyl portions of the (A) and (B) monomers are short chain length alkyls such as $C_1$–$C_8$, preferably $C_1$–$C_5$, more preferably $C_1$–$C_3$, and most preferably $C_1$–$C_2$. When quaternized, the polymers are preferably quaternized with short chain alkyls, i.e., $C_1$–$C_8$, preferably $C_1$–$C_5$, more preferably $C_1$–$C_3$, and most preferably $C_1$–$C_2$. The acid addition salts refer to polymers having protonated amino groups. Acid addition salts can be performed through the use of halogen (e.g. chloride), acetic, phosphoric, nitric, citric, or other acids.

These $(A)_l(B)_m(C)_n$ polymers also comprise a crosslinking agent, which is most typically a material containing two or more unsaturated functional groups. The crosslinking agent is reacted with the monomer units of the polymer and is incorporated into the polymer thereby forming links or covalent bonds between two or more individual polymer chains or between two or more sections of the same polymer chain. Nonlimiting examples of suitable crosslinking agents include those selected from the group consisting of methylenebisacrylamides, diallyldialkyl ammonium halides, polyalkenyl polyethers of polyhydric alcohols, allyl acrylates, vinyloxyalkylacrylates, and polyfunctional vinylidenes. Specific examples of crosslinking agents useful herein include those selected from the group consisting of methylenebisacrylamide, ethylene glycol di-(meth)acrylate, di-(meth)acrylamide, cyanomethylacrylate, vinyloxyethylacrylate, vinyloxyethylmethacrylate, allyl pentaerythritol, trimethylolpropane diallylether, allyl sucrose, butadiene, isoprene, divinyl benzene, divinyl naphthalene, ethyl vinyl ether, methyl vinyl ether, and allyl acrylate. Other crosslinkers include formaldehyde and glyoxal. Preferred for use herein as a crosslinking agent is methylenebisacrylamide.

Widely varying amounts of the crosslinking agent can be employed depending upon the properties desired in the final polymer, e.g. viscosifying effect. Without being limited by theory, it is believed that incorporation of a crosslining agent into these cationic polymers provides a material that is a more effective viscosifying agent without negatives such as stringiness and viscosity breakdown in the presence of electrolytes. The crosslinking agent, when present, can comprise from about 1 ppm to about 1000 ppm, preferably from about 5 ppm to about 750 ppm, more preferably from about 25 ppm to about 500 ppm, even more preferably from about 100 ppm to about 500 ppm, and most preferably from about 250 ppm to about 500 ppm of the total weight of the polymer on a weight/weight basis.

The intrinsic viscosity of the crosslinked polymer, measured in one molar sodium chloride solution at 25° C., is generally above 6, preferably from about 8 to about 14. The molecular weight (weight average) of the crosslinked polymers hereof is high, and is believed to typically be between about 1 million and about 30 million. The specific molecular weight is not critical and lower or higher weight average molecular weights can be used as long as the polymer retains its intended viscosifying effects. Preferably, a 1.0% solution of the polymer (on an actives basis) in deionized water will have a viscosity at 25° C. of at least about 20,000 cP, preferably at least about 30,000 cP, when measured at 20 RPM by a Brookfield RVT (Brookfield Engineering Laboratories, Inc. Stoughton, Mass., USA).

These cationic polymers can be made by polymerization of an aqueous solution containing from about 20% to about 60%, generally from about 25% to about 40%, by weight monomer, in the presence of an initiator (usually redox or thermal) until the polymerization terminates. The crosslinking agent can also be added to the solution of the monomers to be polymerized, to incorporate it into the polymer. In the polymerization reactions, the temperature generally starts between about 0° and 95° C. The polymerization can be conducted by forming a reverse phase dispersion of an aqueous phase of the monomers (and also any additional crosslinking agents) into a nonaqueous liquid, e.g. mineral oil, lanolin, isododecane, oleyl alcohol, and other volatile and nonvolatile esters, ethers, and alcohols, and the like.

All percentages describing the polymer in this section of the description herein are molar, unless otherwise specified. When the polymer contains (C) monomer, the molar proportion of (C) monomer, based on the total molar amount of (A), (B), and (C), can be from 0% to about 99%. The molar proportions of (A) and (B) can each be from 0% to 100%. When acrylamide, is used as the (C) monomer, it will preferably be used at a level of from about 20% to about 99%, more preferably from about 50% to about 90%.

Where monomer (A) and (B) are both present, the ratio of monomer (A) to monomer (B) in the final polymer, on a molar basis, is preferably from about 99:5 to about 15:85, more preferably from about 80:20 to about 20:80. Alternatively, in another class of polymers, the ratio is from about 5:95 to about 50:50, preferably from about 5:95 to about 25:75.

In another alternative class of polymers, the ratio (A):(B) is from about 50:50 to about 85:15. Preferably the ratio (A):(B) is about 60:40 to about 85:15, most preferably about 75:25 to about 85:15.

Most preferred is where monomer (A) is not present and the ratio of monomer (B):monomer (C) is from about 30:70 to about 70:30, preferably from about 40:60 to about 60:40 and most preferably from about 45:55 to about 55:45.

Cationic polymers that are useful herein that are especially preferred are those conforming to the general structure (A)l(B)m(C)n wherein l is zero, (B) is methyl quaternized dimethylaminoethyl methacrylate, the ratio of (B):(C) is from about 45:55 to about 55:45, and the crosslinking agent is methylenebisacrylamide. An example of such a cationic polymer is one that is commercially available as a mineral oil dispersion (which can also include various dispersing aids such as PPG-1 trideceth-6) under the trademark Salcare® SC92 from Allied Colloids Ltd. (Norfolk, Va.). This polymer has the proposed CTFA designation, "Polyquaternium 32 (and) Mineral Oil".

Other cationic polymers useful herein, are those not containing acrylamide or other (C) monomers, that is, n is zero. In these polymers the (A) and (B) monomer components are as described above. An especially preferred group of these non-acrylamide containing polymers is one in which l is also zero. In this instance the polymer is essentially a homopolymer of a dialkylaminoalkyl methacrlyate monomer or its quaternary ammonium or acid addition salt. These diaklylaminoalkyl methacrylate polymers preferably contain a crosslinking agent as described above.

A cationic polymer, which is essentially a homopolymer, useful herein is one conforming to the general structure $(A)_l(B)_m(C)_n$ wherein l is zero, (B) is methyl quaternized dimethylaminoethyl methacrylate, n is zero, and the crosslinking agent is methylenebisacrylamide. An example of such a homopolymer is commercially available as a mixture containing approximately 50% of the polymer, approximately 44% mineral oil, and approximately 6% PPG-l trideceth-6 as a dispersing aid, from Allied Colloids Ltd, (Norfolk, Va.) under the trademark Salcare® SC95. This polymer has recently been given the CTFA designation "Polyquaternium 37 (and) Mineral Oil (and) PPG-1 Trideceth-6".

(iii) Polyacrylamide Polymers

Also useful herein are polyacrylamide polymers, especially non-ionic polyacrylamide polymers including substituted branched or unbranched polymers. These polymers can be formed from a variety of monomers including acrylamide and methacrylamide which are unsubstituted or substituted with one or two alkyl groups (preferably $C_1$ to $C_5$). Preferred are acrylate amide and methacrylate amide monomers in which the amide nitrogen is unsubstituted, or substituted with one or two $C_1$ to $C_5$ alkyl groups (preferably methyl, ethyl, or propyl), for example, acrylamide, methacrylamide, N-methacrylamide, N-methylmethacrylamide, N,N-dimethylmethacrylamide, N-isopropylacrylamide, N-isopropylmethacrylamide, and N,N-dimethylacrylamide. These polymers have a molecular weight greater than about 1,000,000 preferably greater than about 1,5000,000 and range up to about 30,000,000. Most preferred among these polyacrylamide polymers is the non-ionic polymer given the CTFA designation polyacrylamide and isoparaffin and laureth-7, available under the Tradename Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SSS00V, SS500W, SSSA100H, from Lipo Chemicals, Inc., (Patterson, N.J.).

(iv) Polysaccharides

A wide variety of polysaccharides are useful herein. By "polysaccharides" are meant gelling agents containing a backbone of repeating sugar (i.e. carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a C10–C30 straight chain or branched chain alkyl group through an ether linkage. Typically these polymers are ethers of C10–C30 straight or branched chain alcohols with hydroxyalkylcelluloses. Examples of alkyl groups useful herein include those selected from the group consisting of stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1→3) linked glucose units with a (1→6) linked glucose every three units, a commercially available example of which is Clearogel™ CS 11 from Michel Mercier Products Inc. (Mountainside, N.J.).

(v) Gums

Other additional thickening and gelling agents useful herein include materials which are primarily derived from natural sources. Nonlimiting examples of these gelling agent gums include materials selected from the group consisting of acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

(vi) Crosskinked Vinyl Ether/Maleic Anhydride Copolymers

Other additional thickening and gelling agents useful herein include crosslinked copolymers of alkyl vinyl ethers and maleic anhydride. In these copolymers the vinyl ethers are represented by the formula R-O-CH=$CH_2$ wherein R is a C1–C6 alkyl group, preferably R is methyl. Preferred crosslinking agents are C4–C20 dienes, preferably C6 to C16 dienes, and most preferably C8 to C12 dienes. A particularly preferred copolymer is one formed from methyl vinyl ether and maleic anhydride wherein the copolymer has been crosslinked with decadiene, and wherein the polymer when diluted as a 0.5% aqueous solution at pH 7 at 25° C. has a viscosity of 50,000–70,000 cps when measured using a Brookfield RTV viscometer, spindle #7 at 10 rpm. This copolymer has the CTFA designation PVM/MA decadiene crosspolymer and is commercially available as Stabileze™ 06 from International Specialty Products (Wayne N.J.).

(vii) Crosskinked poly-(N-vinylpyrrolidones)

Crosslinked polyvinyl(N-pyrrolidones) useful herein as additional thickening and gelling agents and include those described in U.S. Pat. No. 5,139,770, to Shih et al, issued Aug. 18, 1992, and U.S. Pat. No. 5,073,614, to Shih et al., issued Dec. 17, 1991, both patents of which are incorporated by reference herein in their entirety. These gelling agents typically contain from about 0.25% to about 1% by weight of a crosslinking agent selected from the group consisting of divinyl ethers and dialyl ethers of terminal diols containing from about 2 to about 12 carbon atoms, divinyl ethers and diallyl ethers of polyethylene glycols containing from about 2 to about 600 units, dienes having from about 6 to about 20 carbon atoms, divinyl benzene, vinyl and allyl ethers of pentaerythritol, and the like. Typically, these gelling agents have a viscosity from about 25,000 cps to about 40,000 cps when measured as a 5% aqueous solution at 25° C. using a Brookfield RVT viscometer with Spindle #6 at 10 rpm. Commercially available examples of these polymers include ACP-1 120, ACP-1 179, and ACP-1180, available from International Specialty Products (Wayne, N.J.).

Thickening agents which are suitable for use herein also include those disclosed in U.S. Pat. No. , 4,387,107, to Klein et al., issued Jun. 7, 1983 and "Encyclopedia of Polymer and Thickeners for Cosmetics," R. Y. Lochhead and W. R. Fron, eds., *Cosmetics & Toiletries,* vol. 108, pp. 95–135 (May 1993), which are all incorporated herein by reference in their entirety.

Preferred compositions of the present invention include a thickening agent selected from the group consisting of carboxylic acid polymers, crosslinked polyacrylate polymers, polyacrylamide polymers, and mixtures thereof, more preferably selected from the group consisting of crosslinked polyacrylate polymers, polyacrylamide polymers, and mixtures thereof.

Optional Components

The topical compositions of the present invention may comprise a wide variety of optional components, provided that such optional components are physically and chemically compatible with the essential components described herein, and do not unduly impair stability, efficacy or other use benefits associated with the compositions of the present invention. Optional components may be dispersed, dissolved or the like in the carrier of the present compositions.

Optional components include aesthetic agents and active agents. For example, the compositions may include, in addition to the essential components of the invention, absorbents (including oil absorbents such as clays an polymeric absorbents), abrasives, anticaking agents, antifoaming agents, antimicrobial agents (e.g., a compound capable of destroying microbes, preventing the development of microbes or preventing the pathogenic action of microbes and useful, for example, in controlling acne and/or preserving the topical composition), binders, biological additives, buffering agents, bulking agents, chemical additives, cosmetic biocides, denaturants, cosmetic astringents, drug astringents, external analgesics, film formers, humectants, opacifying agents, fragrances, perfumes, pigments, colorings, essential oils, skin sensates, emollients, skin soothing agents, skin healing agents, pH adjusters, plasticizers, preservatives, preservative enhancers, propellants, reducing agents, skin-conditioning agents, skin penetration enhancing agents, skin protectants, solvents, suspending agents, emulsifiers, thickening agents, solubilizing agents, polymers for aiding the film-forming properties and substantivity of the composition (such as a copolymer of eicosene and vinyl pyrrolidone, an example of which is available from GAF Chemical Corporation as Ganex® V-220), waxes, sunscreens, sunblocks, ultraviolet light absorbers or scattering agents, sunless tanning agents, antioxidants and/or radical scavengers, chelating agents, sequestrants, anti-acne agents, anti-inflammatory agents, anti-androgens, depilation agents, desquamation agents/ exfoliants, organic hydroxy acids, vitamins and derivatives thereof (including water dispersible or soluble vitamins such as Vitamin C and ascorbyl phosphates), compounds which stimulate collagen production, and natural extracts. Such other materials are known in the art. Nonexclusive examples of such materials are described in *Harry's Cosmeticology*, 7th Ed., Harry & Wilkinson (Hill Publishers, London 1982); in *Pharmaceutical Dosage Forms- Disperse Systems;* Lieberman, Rieger & Banker, Vols. 1 (1988) & 2 (1989); Marcel Decker, Inc.; in *The Chemistry and Manufacture of Cosmetics, 2nd. Ed.* deNavarre (Van Nostrand 1962–1965); and in *The Handbook of Cosmetic Science and Technology* 1st Ed. Knowlton & Pearce (Elsevier 1993). can also be used in the present invention.

In a preferred embodiment, the composition also includes an active useful for chronically regulating skin condition. Such materials are those which manifest skin appearance benefits following chronic application of the composition containing such materials. Materials having this effect include, but are not limited to, Vitamin $B_3$ compounds and retinoids.

Specific examples of optional components include the following.

A. Vitamin $B_3$ Compounds

In a preferred embodiment, the compositions of the present invention comprise a safe and effective amount of a vitamin $B_3$ compound. The vitamin $B_3$ compound enhances the skin appearance benefits of the present invention, especially in regulating skin condition, including regulating signs of skin aging, more especially wrinkles, lines, and pores. The compositions of the present invention preferably comprise from about 0.01% to about 50%, more preferably from about 0.1% to about 10%, even more preferably from about 0.5% to about 10%, and still more preferably from about 1% to about 5%, most preferably from about 2% to about 5%, of the vitamin B3 compound.

As used herein, "vitamin $B_3$ compound" means a compound having the formula:

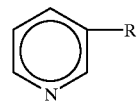

wherein R is —$CONH_2$ (i.e., niacinamide), —COOH (i.e., nicotinic acid) or —$CH_2OH$ (i.e., nicotinyl alcohol); derivatives thereof, and salts of any of the foregoing.

Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide.

Suitable esters of nicotinic acid include nicotinic acid esters of $C_1$–$C_{22}$, preferably $C_1$–$C_{16}$, more preferably $C_1$–$C_6$ alcohols. The alcohols are suitably straight-chain or branched chain, cyclic or acyclic, saturated or unsaturated (including aromatic), and substituted or unsubstituted. The esters are preferably non-vasodilating. As used herein, "non-vasodilating" means that the ester does not commonly yield a visible flushing response after application to the skin in the subject compositions (the majority of the general population would not experience a visible flushing response, although such compounds may cause vasodilation not visible to the naked eye, i.e., the ester is non-rubifacient). Non-vasodilating esters of nicotinic acid include tocopherol nicotinate and inositol hexanicotinate; tocopherol nicotinate is preferred.

Other derivatives of the vitamin $B_3$ compound are derivatives of niacinamide resulting from substitution of one or more of the amide group hydrogens. Nonlimiting examples of derivatives of niacinamide useful herein include nicotinyl amino acids, derived, for example, from the reaction of an activated nicotinic acid compound (e.g., nicotinic acid azide or nicotinyl chloride) with an amino acid, and nicotinyl alcohol esters of organic carboxylic acids (e.g., C1–C18). Specific examples of such derivatives include nicotinuric acid ($C_8H_8N_2O_3$) and nicotinyl hydroxamic acid ($C_6H_6N_2O_2$), which have the following chemical structures:

nicotinuric acid:

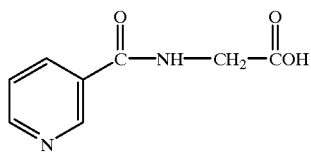

nicotinyl hydroxamic acid:

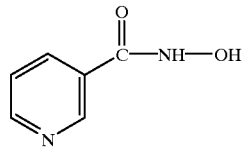

Exemplary nicotinyl alcohol esters include nicotinyl alcohol esters of the carboxylic acids salicylic acid, acetic acid, glycolic acid, palmitic acid and the like. Other non-limiting examples of vitamin $B_3$ compounds useful herein are 2-chloronicotinamide, 6-aminonicotinamide, 6-methylnicotinamide, n-methyl-nicotinamide, n,n-diethylnicotinamide, n-(hydroxymethyl)-nicotinamide, quinolinic acid imide, nicotinanilide, n-benzylnicotinamide, n-ethylnicotinamide, nifenazone, nicotinaldehyde, isonicotinic acid, methyl isonicotinic acid, thionicotinamide, nialamide, 1-(3-pyridylmethyl) urea, 2-mercaptonicotinic acid, nicomol, and niaprazine.

Examples of the above vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company milwaukee, Wis.).

One or more vitamin $B_3$ compounds may be used herein. Preferred vitamin $B_3$ compounds are niacinamide and tocopherol nicotinate. Niacinamide is more preferred.

When used, salts, derivatives, and salt derivatives of niacinamide are preferably those having substantially the same efficacy as niacinamide in the methods of regulating skin condition described herein.

Salts of the vitamin $B_3$ compound are also useful herein. Nonlimiting examples of salts of the vitamin $B_3$ compound useful herein include organic or inorganic salts, such as inorganic salts with anionic inorganic species (e.g., chloride, bromide, iodide, carbonate, preferably chloride), and organic carboxylic acid salts (including mono-, di- and tri- C1–C18 carboxylic acid salts, e.g., acetate, salicylate, glycolate, lactate, malate, citrate, preferably monocarboxylic acid salts such as acetate). These and other salts of the vitamin $B_3$ compound can be readily prepared by the skilled artisan, for example, as described by W. Wenner, "The Reaction of L-Ascorbic and D-Iosascorbic Acid with Nicotinic Acid and Its Amide", J. Organic Chemistry, VOL. 14, 22–26 (1949), which is incorporated herein by reference. Wenner describes the synthesis of the ascorbic acid salt of niacinamide.

In a preferred embodiment, the ring nitrogen of the vitamin $B_3$ compound is substantially chemically free (e.g., unbound and/or unhindered), or after delivery to the skin becomes substantially chemically free ("chemically free" is hereinafter alternatively referred to as "uncomplexed"). More preferably, the vitamin $B_3$ compound is essentially uncomplexed. Therefore, if the composition contains the vitamin $B_3$ compound in a salt or otherwise complexed form, such complex is preferably substantially reversible, more preferably essentially reversible, upon delivery of the composition to the skin. For example, such complex should be substantially reversible at a pH of from about 5.0 to about 6.0. Such reversibility can be readily determined by one having ordinary skill in the art.

More preferably the vitamin $B_3$ compound is substantially uncomplexed in the composition prior to delivery to the skin. Exemplary approaches to minimizing or preventing the formation of undesirable complexes include omission of materials which form substantially irreversible or other complexes with the vitamin $B_3$ compound, pH adjustment, ionic strength adjustment, the use of surfactants, and formulating wherein the vitamin $B_3$ compound and materials which complex therewith are in different phases. Such approaches are well within the level of ordinary skill in the art.

Thus, in a preferred embodiment, the vitamin $B_3$ compound contains a limited amount of the salt form and is more preferably substantially free of salts of a vitamin $B_3$ compound. Preferably the vitamin $B_3$ compound contains less than about 50% of such salt, and is more preferably essentially free of the salt form. The vitamin $B_3$ compound in the compositions hereof having a pH of from about 4 to about 7 typically contain less than about 50% of the salt form.

The vitamin $B_3$ compound may be included as the substantially pure material, or as an extract obtained by suitable physical and/or chemical isolation from natural (e.g., plant) sources. The vitamin $B_3$ compound is preferably substantially pure, more preferably essentially pure.

B. Retinoids

In a preferred embodiment, the compositions of the present invention contain a retinoid. The retinoid enhances the skin appearance benefits of the present invention, especially in regulating skin condition, including regulating signs of skin aging, more especially wrinkles, lines, and pores.

As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., $C_2$–$C_{22}$ alkyl esters of retinol, including retinyl palmitate, retinyl acetate, retinyl propionate), retinal, and/or retinoic acid (including all-trans retinoic acid and/or 13-cisretinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. Nos. 4,677,120, issued Jun. 30, 1987 to Parish et al.; 4,885,311, issued Dec. 5, 1989 to Parish et al.; 5,049,584, issued Sep. 17, 1991 to Purcell et al.; 5,124,356, issued Jun. 23, 1992 to Purcell et al.; and Reissue 34,075, issued Sep. 22, 1992 to Purcell et al.. Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). One or more retinoids may be used herein. Preferred retinoids are retinol, retinyl palmitate, retinyl acetate, retinyl proprionate, retinal and combinations thereof. More preferred are retinol and retinyl palmitate.

The retinoid may be included as the substantially pure material, or as an extract obtained by suitable physical and/or chemical isolation from natural (e.g., plant) sources. The retinoid is preferably substantially pure, more preferably essentially pure.

The compositions of this invention may contain a safe and effective amount of the retinoid, such that the resultant composition is safe and effective for regulating skin condition, preferably for regulating visible and/or tactile discontinuities in skin, more preferably for regulating signs of skin aging, even more preferably for regulating visible and/or tactile discontinuities in skin texture associated with skin aging. The compositions preferably contain from or about 0.005% to or about 2%, more preferably 0.01% to or about 2%, retinoid. Retinol is most preferably used in an amount of from or about 0.01% to or about 0.15%; retinol esters are most preferably used in an amount of from or about 0.01% to or about 2% (e.g., about 1%); retinoic acids are most preferably used in an amount of from or about 0.01% to or about 0.25%; tocopheryl-retinoate, adapalene, and tazarotene are most preferably used in an amount of from or about 0.01% to or about 2%.

In a preferred embodiment, the composition contains both a retinoid and a Vitamin $B_3$ compound. The retinoid is preferably used in the above amounts, and the vitamin $B_3$ compound is preferably used in an amount of from or about 0.1% to or about 10%, more preferably from or about 2% to or about 5%.

C. Anti-Inflammatory Agents

A safe and effective amount of an anti-inflammatory agent may be added to the compositions of the subject invention, preferably from about 0.1% to about 10%, more preferably from about 0.5% to about 5%, of the composition. The anti-inflammatory agent enhances the skin appearance benefits of the present invention, e.g., such agents contribute to a more uniform and acceptable skin tone or color. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc. of non-steroidal anti-inflammatory agents, reference may be had to standard texts, including *Anti-inflammatory and Anti-Rheumatic Drugs*. K. D. Rainsford, Vol. I–III, CRC Press, Boca Raton, (1985), and *Anti-inflammatory Agents, Chemistry and Pharmacology*, 1, R. A. Scherrer, et al., Academic Press, New York (1974), each incorporated herein by reference.

Specific non-steroidal anti-inflammatory agents useful in the composition invention include, but are not limited to:

1) the oxicams, such as piroxicam, isoxicam, tenoxicam, sudoxicam, and CP-14,304;

2) the salicylates, such as aspirin, disalcid, benorylate, trilisate, safapryn, solprin, diflunisal, and fendosal;

3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac;

4) the fenamates, such as mefenamic, meclofenamic, flufenamic, niflumic, and tolfenamic acids;

5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and 6) the pyrazoles, such as phenylbutazone, oxyphenbutazone, feprazone, azapropazone, and trimethazone.

Mixtures of these non-steroidal anti-inflammatory agents may also be employed, as well as the dermatologically acceptable salts and esters of these agents. For example, etofenamate, a flufenamic acid derivative, is particularly useful for topical application. Of the nonsteroidal anti-inflammatory agents, ibuprofen, naproxen, flufenamic acid, etofenamate, aspirin, mefenamic acid, meclofenamic acid, piroxicam and felbinac are preferred; ibuprofen, naproxen, etofenamate, aspirin and flufenamic acid are most preferred.

Finally, so-called "natural" anti-inflammatory agents are useful in methods of the subject invention. Such agents may suitably be obtained as an extract by suitable physical and/or chemical isolation from natural sources (e.g., plants, fungi, by-products of microorganisms). For example, candelilla wax, alpha bisabolol, aloe vera, Manjistha (extracted from plants in the genus Rubia, particularly *Rubia Cordifolia*), and Guggal (extracted from plants in the genus Commiphora particularly *Commiphora Mukul*), kola extract, chamomile, and sea whip extract, may be used.

Additional anti-inflammatory agents useful herein include compounds of the Licorice (the plant genus/species *Glycyr-*

*rhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$–$C_{24}$ saturated or unsaturated esters of the acids, preferably $C_{10}$–$C_{24}$, more preferably $C_{16}$–$C_{24}$. Specific examples of the foregoing include oil soluble licorice extract the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate. Stearyl glycyrrhetinate is preferred.

D. Sunscreens and Sunblocks

Exposure to ultraviolet light can result in excessive scaling and texture changes of the stratum corneum. Therefore, the compositions of the subject invention preferably contain a sunscreen or sunblock. Suitable sunscreens or sunblocks may be organic or inorganic.

A wide variety of conventional sunscreening agents are suitable for use herein. Sagarin, et al., at Chapter VIII, pages 189 et seq., of *Cosmetics Science and Technology* (1972) discloses numerous suitable agents, and is incorporated herein by reference. Specific suitable sunscreening agents include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-propyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoyl-methane; etocrylene; octocrylene; [3-(4'-methylbenzylidene bornan-2-one) and 4-isopropyl-di-benzoylmethane.

Of these, 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone, octyldimethyl-p-aminobenzoic acid, digalloyltrioleate, 2,2-dihydroxy4-methoxybenzophenone, ethyl-4-(bis(hydroxypropyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene and mixtures of these compounds, are preferred.

More preferred organic sunscreens useful in the compositions useful in the subject invention are 2-ethylhexyl-p-methoxycinnamate, butylmethoxydibenzoyl-methane, 2-hydroxy4-methoxybenzo-phenone, 2-phenylbenzimidazole-5-sulfonic acid, octyldimethyl-p-aminobenzoic acid, octocrylene and mixtures thereof.

Also particularly useful in the compositions are sunscreens such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991, both of which are incorporated herein by reference. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methyl-aminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methyl-aminobenzoic acid ester with 4-hydroxydibenzoylmethane; 4-N,N-(2-ethylhexyl)methyl-aminobenzoic acid ester of 2-hydroxy-4-(2-hydroxyethoxy) benzophenone; 4-N,N-(2-ethylhexyl)-methylaminobenzoic acid ester of 4-(2-hydroxyethoxy)dibenzoylmethane; N,N-di-(2-ethylhexyl)-4-aminobenzoic acid ester of 2-hydroxy4-(2-hydroxyethoxy)benzophenone; and N,N-di-(2-ethylhexyl)-4-aminobenzoic acid ester of 4-(2-hydroxyethoxy)dibenzoylmethane and mixtures thereof.

Especially preferred sunscreens or sunblocks include butylmethoxydibenzoylmethane, 2-ethylhexyl-p-methoxycinnamate, phenyl benzimidazole sulfonic acid, and octocrylene.

A safe and effective amount of the sunscreen or sunblock is used, typically from about 1% to about 20%, more typically from about 2% to about 10%. Exact amounts will vary depending upon the sunscreen chosen and the desired Sun Protection Factor (SPF).

An agent may also be added to any of the compositions useful in the subject invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

E. Anti-Oxidants/Radical Scavengers

Preferred compositions of the subject invention include an anti-oxidant/radical scavenger. The anti-oxidant/radical scavenger is especially useful for providing protection against UV radiation which can cause increased scaling or texture changes in the stratum corneum and against other environmental agents which can cause skin damage.

A safe and effective amount of an anti-oxidant/radical scavenger may be added to the compositions of the subject invention, preferably from about 0.1% to about 10%, more preferably from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, lysine, methionine, proline, superoxide dismutase, silymarin, tea extracts, grape skin/seed extracts, melanin, and rosemary extracts may be used. Preferred anti-oxidants/radical scavengers are selected from tocopherol sorbate and other esters of tocopherol, more preferably tocopherol sorbate. For example, the use of tocopherol sorbate in topical compositions and applicable to the present invention is described in U.S. Pat. No. 4,847,071, issued on Jul. 11, 1989 to Donald L. Bissett, Rodney D. Bush and Ranjit Chatterjee, incorporated herein by reference.

F. Chelators

As used herein, "chelating agent" means an active agent capable of removing a metal ion from a system by forming a complex so that the metal ion cannot readily participate in or catalyze chemical reactions. The inclusion of a chelating agent is especially useful for providing protection against UV radiation which can contribute to excessive scaling or skin texture changes and against other environmental agents which can cause skin damage.

A safe and effective amount of a chelating agent may be added to the compositions of the subject invention, preferably from about 0.1% to about 10%, more preferably from about 1% to about 5%, of the composition. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995; all incorporated herein by reference. Preferred chelators useful in compositions of the subject invention are furildioxime and derivatives thereof.

G. Organic Hydroxy Acids

Compositions of the present invention may comprise an organic hydroxy acid. Suitable hydroxy acids include $C_1$–$C_{18}$ hydroxy acids, preferably $C_8$ or below. The hydroxy acids can be substituted or unsubstituted, straight chain, branched chain or cyclic (preferably straight chain), and saturated or unsaturated (mono- or poly-unsaturated) (preferably saturated). Non-limiting examples of suitable hydroxy acids include salicylic acid, glycolic acid, lactic acid, 5 octanoyl salicylic acid, hydroxyoctanoic acid, hydroxycaprylic acid, and lanolin fatty acids. Preferred concentrations of the organic hydroxy acid range from about 0.1% to about 10%, more preferably from about 0.2% to about 5%, also preferably from about 0.5% to about 2%. Salicylic acid is preferred. The organic hydroxy acids enhance the skin appearance benefits of the present invention. For example, the organic hydroxy acids tend to improve the texture of the skin.

H. Desquamation Agents/Exfoliants

A safe and effective amount of a desquamation agent may be added to the compositions of the subject invention, more preferably from about 0.1% to about 10%, even more preferably from about 0.2% to about 5%, also preferably from about 0.5% to about 4% of the composition. Desquamation agents enhance the skin appearance benefits of the present invention. For example, the desquamation agents tend to improve the texture of the skin (e.g., smoothness). A variety of desquamation agents are known in the art and are suitable for use herein, including but not limited to the organic hydroxy agents described above. One desquamation system that is suitable for use herein comprises sulfihydryl compounds and zwitterionic surfactants and is described in copending application Ser. No. 08/480,632, filed on Jun. 7, 1995 in the name of Donald L. Bissett, corresponding to PCT Application No. U.S. 95/08136, filed Jun. 29, 1995, each incorporated herein by reference. Another desquamation system that is suitable for use herein comprises salicylic acid and zwitterionic surfactants and is described in copending patent application Ser. No. 08/554,944, filed on Nov. 13, 1995 as a continuation of Ser. No. 08/209,401, filed on Mar. 9, 1994 in the name of Bissett, corresponding to PCT Application No. 94/12745, filed 11/4/94, published May 18, 1995, each incorporated herein by reference. Zwitterionic surfactants such as described in these applications are also useful as desquamatory agents herein, with cetyl betaine being particularly preferred.

I. Skin Lightening Agents

The compositions of the present invention may comprise a skin lightening agent. When used, the compositions preferably comprise from about 0.1% to about 10%, more preferably from about 0.2% to about 5%, also preferably from about 0.5% to about 2%, of a skin lightening agent. Suitable skin lightening agents include those known in the art, including kojic acid, arbutin, ascorbic acid and derivatives thereof, e.g., magnesium ascorbyl phosphate. Skin lightening agents suitable for use herein also include those described in copending patent application Ser. No. 08/479,935, filed on Jun. 7, 1995 in the name of Hillebrand, corresponding to PCT Application No. U.S. 95/07432, filed Jun. 12, 1995; and copending patent application Ser. No. 08/390,152, fled on Feb. 24, 1995 in the names of Kalla L. Kvalnes, Mitchell A. DeLong, Barton J. Bradbury, Curtis B. Motley, and John D. Carter, corresponding to PCT Application No. U.S. 95/02809, filed Mar. 1, 1995, published Sep. 8, 1995; all incorporated herein by reference.

J. Skin Conditioners

Preferred compositions of the invention comprise an optional skin conditioning component comprising one or more skin conditioning compounds. The skin conditioning component is useful for lubricating the skin, increasing the smoothness and suppleness of the skin, preventing or relieving dryness of the skin, hydrating the skin, and/or protecting the skin. The skin conditioning component enhances the skin appearance improvements of the present invention, including but not limited to essentially immediate visual improvements in skin appearance. The skin conditioning component is preferably selected from the group consisting of emollients, humectants, moisturizers and mixtures thereof. The skin conditioning component is preferably present at a level of at least about 0.1%, more preferably from about 1% to about 99%, even more preferably from about 1% to about 50%, still more preferably from about 2% to about 30% and most preferably from about 5% to about 25% (e.g., about 5% to about 10% or 15%). Compositions containing the skin conditioning component tend to have the preferred Hydration Factors described herein.

A variety of emollients may be employed. These emollients may be selected from one or more of the following classes: Triglyceride esters which include, but are not limited to, vegetable and animal fats and oils such as castor oil, cocoa butter, safflower oil, cottonseed oil, corn oil, olive oil, cod liver oil, almond oil, avocado oil, palm oil, sesame oil, squalene, kikui oil and soybean oil; Acetoglyceride esters, such as acetylated monoglycerides; Ethoxylated glycerides, such as ethoxylated glyceryl monostearate; Alkyl esters of fatty acids having 10 to 20 carbon atoms which include, but are not limited to, methyl, isopropyl, and butyl esters of fatty acids such as hexyl laurate, isohexyl laurate, isohexyl palmitate, isopropyl palmitate, methyl palmitate, decyloleate, isodecyl oleate, hexadecyl stearate decyl stearate, isopropyl isostearate, methyl isostearate, diisopropyl adipate, diisohexyl adipate, dihexyldecyl adipate, diisopropyl sebacate, lauryl lactate, myristyl lactate, and cetyl lactate; Alkenyl esters of fatty acids having 10 to 20 carbon atoms such as oleyl myristate, oleyl stearate, and oleyl oleate; Fatty acids having 10 to 20 carbon atoms such as pelargonic, lauric, myristic, palmitic, stearic, isostearic, hydroxystearic, oleic, linoleic, ricinoleic, arachidic, behenic, and erucic acids; Fatty alcohols having 10 to 20 carbon atoms such as lauryl, myristyl, cetyl, hexadecyl, stearyl, isostearyl, hydroxystearyl, oleyl, ricinoleyl, behenyl, erucyl, and 2-octyl dodecanyl alcohols; Lanolin and lanolin derivatives such as lanolin, lanolin oil, lanolin wax, lanolin alcohols, lanolin fatty acids, isopropyl lanolate, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, and liquid and semisolid lanolin absorption bases; Polyhydric alcohol esters such as ethylene glycol mono and di-fatty acid esters, diethylene glycol mono-and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol polyfatty esters, ethoxylated glyceryl monostearate, 1,2-butylene glycol monostearate, 1,2-butylene glycol distearate, sorbitan fatty acid esters, and polyoxyethylene sorbitan fatty acid esters; Wax esters such as beeswax, spermaceti, myristyl myristate, stearyl stearate; Beeswax derivatives such as polyoxyethylene sorbitol beeswax which are reaction products of beeswax with ethoxylated sorbitol of varying ethylene oxide content, forming a mixture of ether esters; Vegetable waxes including, but not limited to, carnauba and candelilla waxes; Phospholipids such as lecithin and derivatives; Sterols including, but not limited to, cholesterol and cholesterol fatty acid esters; and Amides such as fatty acid amides, ethoxylated fatty acid amides, and solid fatty acid alkanolamides.

Additional types of conditioning compounds are humectants of the polyhydric alcohol-type. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, erythritol, threitol, pentaerythritol, xylitol, glucitol, mannitol, hexylene glycol, butylene glycol (e.g., 1,3-butylene glycol), hexane triol (e.g., 1,2,6-hexanetriol), glycerol, ethoxylated glycerol, propoxylated glycerol, sodium 2-pyrrolidone-5-carboxylate, soluble collagen, dibutyl phthalate, gelatin and mixtures thereof.

Also useful herein are guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); sugar and starch derivatives (e.g., alkoxylated glucose); hyaluronic acid and derivatives thereof (e.g., salt derivatives such as sodium hyaluraonate); lactamide monoethanolamine; acetamide monoethanolamine; urea; panthenol; sugars; starches; silicone fluids; silicone gums; and mixtures thereof. Also useful are the propoxylated glycerols described in U.S. Pat. No. 4,976,953, which is description is incorporated herein by reference. Other useful conditioning compounds include the various $C_1$–$C_{30}$ monoesters and polyesters of sugars and related materials such as described herein in reference to the hydrophobic component.

The above listed compounds may be incorporated singly or in combination.

Preparation of Compositions

The compositions of the present invention are generally prepared by conventional methods such as are known in the art of making topical compositions. Such methods typically involve mixing of the ingredients in one or more steps to a relatively uniform state, with or without heating, cooling, application of vacuum, and the like.

Properties of the compositions

The compositions of the present invention are characterized by their Contrast Ratio and % Transmittance or Coverage Index. The compositions may be further characterized by their Apparent Viscosity and/or Hydration Factor.

a) Contrast Ratio

Compositions of the present invention have a contrast ratio of from about 9 to about 30, more preferably from about 11 to about 22. Contrast ratio can be determined by the following Contrast Ratio Method, using an opacity chart (form 2A, Leneta Company of Manwah, N.J. or the equivalent thereof), and a chromameter (e.g., a Minolta CR-200 Chromameter, d65 illuminant, 0 degree viewing angle, equipped with a specular component, commercially available from the Minolta Camera Co. of Ramsey, N.J. and described in the chromameter manual, version 3.0; 1988, incorporated herein by reference, or the equivalent thereof).

The opacity chart is half black (top) and half white (bottom), with the colors being separated along a line parallel to the horizon. 4 grams of a test product are applied in about a ½"×3" area at the top of the opacity chart. The product is drawn down the length of the card, through both halves and generally symmetrically, into a thin film using a 1.5 mil film applicator (e.g., as commercially available from BYK Gardner of Columbia, Md., or the equivalent thereof. The film is allowed to dry for 24 hours under conditions of 25° C. ±1° C., 1 atm.

Using the chromameter, the Y tristimulus value (i.e., the XYZ color space of the film) of the product film is measured and recorded. The Y tristimulus value is measured in three different areas of the product film over the black section of the opacity chart, and also in three different areas of the product film over the white section of the opacity chart. Areas which are measured are those having an even distribution of product over the area.

The contrast ratio is calculated as the mathematical average of the three Y tristimulus values over the black areas, divided by the mathematical average of the three Y tristimulus values over the white areas, times 100:

$$\text{Contrast Ratio} = \frac{\text{average(three } Y_{\text{black}})}{\text{average(three } Y_{\text{white}})} \times 100$$

b) % Transmittance and Coverage Index

Compositions of the present invention have a % transmittance of about 92% to about 62%, more preferably from about 85% to about 75%, and a coverage index of from about 6 to about 30, more preferably from about 10 to about 20. Coverage index and % transmittance can be determined by the following Coverage Method.

The determination of % transmission and coverage index involves measuring the transmission of light through a collagen film to which product has been applied, relative to a control film. The methodology requires a light source sufficiently powerful for sample illumination, a camera and video frame grabber for capturing the image of the sample on the collagen surface and a computer with video imaging software for data analysis and for viewing on a video monitor. Suitable image capture and analysis software includes Optimas 5.2 from Optimas Corp., Washington (refer to Image Analysis Software guide Volume I), the software and guide being incorporated herein by reference.

Using a collagen film (such as IMS #1192 or equivalent available from IMS Inc. Milford Conn.) mounted in a suitable holder, apply 40 microliters (using a Microman M50 pipette) of product and spread evenly by hand on the film surface using 10 finger rotations. Optionally, the sample is mounted on a Zeiss SV-11 microscope (or equivalent) equipped with a 1X lens (the microscope is useful for enlarging the image which the camera is capturing; the effective magnification of this system is about 5 microns/pixel). A mounting template can optionally be employed to aid in repositioning the sample for multiple measurements. The SV-11 should be set up so that maximum light is being transmitted to the camera (e.g., a Sony 760-MD CCD 3 Camera). To insure proper positioning and a clear image, the equipment is set in the following manner. Camera controls are set so that the Gamma and Linear matrix switches are off. The camera control box settings are further defined as follows: Gain=0, White/Black balance on auto, iris- auto, mode-camera, detail-12 o'clock position, phase-0 degrees, SC-3 o'clock position, H-12 o'clock position, Color temp - 3200K, shutter off. The camera should be allowed to warm up for 15 minutes before adjusting white and black balance. Press the button labeled "white" to adjust the white balance, and adjust black balance by pulling the black adjustment rod and pushing the button that says black. Computer cables are connected to the RGB1 and Composite Sync.ports on the camera. The microscope Iris is set to completely open and a frosted glass plate is positioned in the microscope base for a uniformly lit field. A clear glass plate may optionally be used to adjust the sample height. Open the Optimas 5.2 program on the computer. Use a sample cup which is partially covered with black tape in the light path to adjust gain and offset (brightness). The reflecting mirror at the base of the microscope is set for maximum reflection into the microscope. The mean of the light source should be 245 to 254.5. The STD Deviation should be less than 3. If the mean is out of specifications check the light bulb alignment and mirror adjustment.

For the control, an untreated piece of collagen firm (such as IMS #1192 available from IMS Inc. Milford Conn.), is mounted on a sample cup which is placed on the microscope such that the film lies in the center of the light path. The film is focused and light transmission through the film is measured using the image capture and analysis software. Multiple measurements are taken from separate areas of the sample, repositioning and refocusing the film for each measurement (seven or more measurements are taken). The histogram mean and standard deviation are determined using the image capture and analysis software.

For measuring light transmission by the test product, a piece of collagen film is first pre-hydrated with distilled water to insure flexibility. 40 microliters of test product is then dispensed on the film (e.g., using a Microman M50 pipette or equivalent), and spread evenly over its surface to produce an even film covering the surface of the collagen (generally by lightly spreading the material by applying 10 rotations of the finger, wearing a clean, latex finger cot, to the material). After waiting for a period of 5 minutes, the sample is mounted on the microscope base. Light transmission measurements through the film and product are then taken in the manner described for the control.

Least significant differences can be performed on the data using Fischer's LSD method.

The coverage index and % transmission are calculated as follows:

Coverage Index=Control Mean–Test Product Mean/Control Mean× 100

%Transmission=100–Coverage Index c) Apparent Viscosity

Preferred compositions have an apparent viscosity of from about 5,000 to about 200,000 centipoise (cps), for example, from about 20,000 to about 150,000 cps, from about 25,000 to about 100,000 cps, or from about 40,000 to about 70,000 cps (e.g, about 60,000 cps). Nonlimiting exemplary lotions have an apparent viscosity of from about 10,000 to about 40,000 cps; nonlimiting exemplary creams have an apparent viscosity of from about 60,000 to about 160,000 cps. Apparent viscosity can be determined using a Brookfield DVII RV viscometer, spindle TD, at 5rpm, or the equivalent thereof. The viscosity is determined on the composition after the composition has been allowed to stabilize following its preparation, generally at least 24 hours under conditions of 25° C. ±1° C. and ambient pressure after preparation of the composition. Apparent viscosity is measured with the composition at a temperature of 25° C.±1° C., after 30 seconds spindle rotation.

d) Hydration Factor

Preferred compositions of the present invention have a Hydration Factor of at least zero as measured by the Skin Moisturizer Hydration Test. The Skin Moisturizer Hydration Test evaluates and compares the in-vivo, hydration efficacy of topical compositions. The test method utilizes a Courage and Khazaka Comeometer 820 PC to measure the electrical capacitance of the skin surface. Without being limited by theory, it is believed that the electrical capacitance is an indirect measurement of water presence and therefore skin surface hydration.

The Skin Moisturizer Hydration Test is determined using at least 16 subjects in general good health (free of medical conditions, adverse reactions or sensitivities which might affect the skin test results). In general, the products to be tested are applied to the forearms of each subject, in an area not having excessive amounts of hair, dermatitis or scars. More specifically, at least two, 3×4 $cm^2$, test regions are identified on the volar region of the same forearm. The composition of the present invention is applied to one test region (3 $\mu l/cm^2$) and a reference (or control) composition is applied to the other test region (3 $\mu l/cm^2$).

An oil-in-water emulsion providing a specific level of hydration and having the following formulation is used as the reference composition:

|  | Ingredient (CTFA Name as applicable) | Weight % |
| --- | --- | --- |
| PHASE A: | Water U.S.P. | 78.96 |
|  | Disodium EDTA | 0.15 |
|  | Glycerin | 5 |
| PHASE B: | Cetyl hydroxy ethyl cellulose | 0.15 |
|  | Methyl Paraben | 0.25 |
| PHASE C: | Cetyl Alcohol | 0.5 |
|  | Stearyl Alcohol | 0.5 |
|  | Behenyl Alcohol | 0.5 |

-continued

| | Ingredient (CTFA Name as applicable) | Weight % |
|---|---|---|
| | Cetyl ricinoleate | 3 |
| | Steareth-2 (Brij 72) | 1.05 |
| | Distearyldimonium chloride (Varisoft TA-100) | 0.25 |
| | Propyl Paraben | 0.10 |
| | Myristyl myristate | 1.5 |
| | Caprylic/Capritryglycerides | 1.5 |
| | Mineral oil | 2 |
| | Fatty acid ester of sugar* | 1 |
| | Polypropylene glycol-15 stearyl ether (Arlamol E) | 1.05 |
| PHASE D: | dimethicone 10 cst (Dow Corning) | 2 |
| PHASE E: | Benzyl Alcohol | 0.5 |
| PHASE F: | 50% NaOH | 0.04 |

*A C1–C30 monoester of polyester of sugars and one or more carboxylic acid moieties as described Blend the A phase components with a suitable mixer (e.g., Tekmar model RW2ODZ2), heating while stirring to a temperature of about 70–80° C. Add the cetyl hyroxy ethyl cellulose and methyl paraben with mixing at about 70–80° C. to melt the components. Separately, blend the C phase components and mill to obtain an acceptably smooth mixture (e.g., using a Tekmar T50 Mill). Add the C phase mixture to the above mixture and mix. Remove the combination from the bath, with continued stirring, once the temperature reaches about 45° C. Add the dimethicone and mix. Add and mix in the benzyl alcohol, then the NaOH. Adjust the pH as necessary to 7.

Test Method: Apply the composition to the subject's skin as described above. Spread the composition on the test region by rubbing in a circular motion, using a cotted finger until the product has blended into the skin completely. Take electrical capacitance values with the corneometer at baseline (before product application) and then 3 hours, and 6 hours after product application. The corneometer probe should be wiped clean before each test site reading using a non-linting material such as a Kimwipe and zeroed against a dry clean surface to test the integrity of the system.

For each subject, hydration measurements on treated sites will be baseline subtracted (the resulting values being referred to as "measurement unit"). A multi-factor analysis of variance using Fischer's least significant difference analysis should be applied to compare data between products.

A comparatively higher corneometer reading indicates higher skin surface capacitance and therefore higher skin surface water content or hydration. The difference between the corneometer values of reference composition and the test formulation (which have been baseline adjusted) is the Hydration Factor and is illustrated by the following formula:

Hydration Factor=("Measurement Unit"$_{test\ formulation}$)−("Measurement Unit"$_{reference\ formulation}$)

Preferred compositions of the present invention have a Hydration Factor of greater than about 0, preferably about 1.5 or more, more preferably about 2 or more.

Methods for Regulating Skin Condition

The compositions of the present invention are useful for regulating mammalian skin condition (especially human skin, more especially human facial skin), including regulating visible and/or tactile discontinuities in skin, e.g., visible and/or tactile discontinuities in skin texture, more especially discontinuities associated with skin aging.

A wide range of quantities of the compositions of the present invention can be employed to provide a skin appearance and/or feel benefit. Quantities of the present compositions which are typically applied per application are, in mg composition/cm$^2$ skin, from about 0.1 mg/cm$^2$ to about 10 mg/cm$^2$. A particularly useful application amount is about 2 mg/cm$^2$. Typically applications would be on the order of about once per day, however application rates can vary from about once per week up to about three times per day or more.

The compositions of this invention provide a visible improvement in skin condition essentially immediately following application of the composition to the skin. Such immediate improvement involves coverage or masking of skin imperfections such as textural discontinuities (including those associated with skin aging, such as enlarged pores), and/or providing a more even skin tone or color.

In a preferred embodiment, the composition includes an active which chronically regulates skin condition and is topically applied chronically. "Chronic topical application" and the like involves continued topical application of the composition over an extended period during the subject's lifetime, preferably for a period of at least about one week, more preferably for a period of at least about one month, even more preferably for at least about three months, even more preferably for at least about six months, and more preferably still for at least about one year. Chronic regulation of skin condition involves improvement of skin condition following multiple topical applications of the composition to the skin. While benefits are obtainable after various maximum periods of use (e.g., five, ten or twenty years), it is preferred that chronic application continue throughout the subject's lifetime. Typically applications would be on the order of about once per day over such extended periods, however application rates can vary from about once per week up to about three times per day or more. Regulating skin condition involves topically applying to the skin a safe and effective amount of a composition of the present invention. The amount of the composition which is applied, the frequency of application and the period of use will vary widely depending upon the active levels of a given composition and the level of regulation desired, e.g., in light of the level of skin aging present in the subject and the rate of further skin aging.

Regulating skin condition is preferably practiced by applying a composition in the form of a skin lotion, cream, cosmetic, or the like which is intended to be left on 5 the skin for an extended period, for some esthetic, prophylactic, therapeutic or other benefit (i.e., a "leave-on" composition). As used herein, "leave-on" compositions exclude rinse-off skin cleansing products. After applying the composition to the skin, the leave-on composition is preferably left on the skin for a period of at least about 15 minutes, more preferably at least about 30 minutes, even more preferably at least about 1 hour, most preferably for at least several hours, e.g., up to about 12 hours.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are given in CTFA name.

Examples 1–3

Oil-in-water emulsions are prepared from the following ingredients using conventional formulating techniques.

|         |                        | Ex 1    | Ex 2    | Ex 3    |
|---------|------------------------|---------|---------|---------|
| Phase A | distilled water        | qs 100  | qs 100  | qs 100  |
| Phase B | Glycerin               | 5       | 5       | 5       |
|         | TiO$_2$                | 0.75    | 0.75    | 0 75    |
| Phase C | glycerin               | 1       | 1       | 1       |
|         | EDTA                   | 0.1     | 0.1     | 0.1     |
|         | Carbopol 954           | 0.68    | 0.5     | 0.5     |
|         | Carbopol 1382          | 0.1     | 0.1     | 0.1     |
| Phase D | Cetyl Alcohol          | 0.72    | 0.72    | 0.72    |
|         | Stearyl Alcohol        | 0.48    | 0.48    | 0.48    |
|         | Stearic Acid           | 0.1     | 0.1     | 0.1     |
|         | PEG-100 Stearate       | 0.1     | 0.1     | 0.1     |
|         | Arlatone 2121          | 1       | 1       | 1       |
|         | Silicone Q21403        | 2       | 2       | 2       |
|         | Fatty acid ester of sugar[1] | 0.67 | 0.67 | 0.67 |
|         | Tocopherol Acetate     | 0       | 0       | 0.5     |
|         | Niacinamide            | 2       | 2       | 2       |
| Phase E | distilled water        | 2       | 2       | 2       |
|         | NaOH                   | to neutralize Carbopols | to neutralize Carbopols | to neutralize Carbopols |
| Phase F | Urea                   | 2       | 0       | 0       |
|         | D-Panthenol            | 0       | 0       | 0.5     |
|         | distilled water        | 5       | 5       | 5       |
| Phase G | Glydant Plus           | 0.1     | 0.1     | 0.1     |
|         | Glycerin               | 1       | 1       | 1       |
|         | distilled water        | 1       | 1       | 1       |
| Phase H | Methyl Isostearate     | 1.33    | 0       | 0       |
|         | Isopropyl Isostearate  | 0       | 1.33    | 1.33    |
|         | Retinol                | 0       | 0       | 0.04    |
|         | BHT                    | 0       | 0       | 0.05    |
|         | Tween 20               | 0       | 0       | 0.04    |

[1] A C1–C30 monoester or polyester of sugars and one or more carboxylic acid moieties as described herein, preferably a sucrose polyester in which the degree of esterification is 7–8, and in which the fatty acid moieties are C18 mono- and/or di-unsaturated and behenic, in a molar ratio of unsaturates:behenic of 1:7 to 3:5, more preferably the octaester of sucrose in which there are about 7 behenic fatty acid moieties and about 1 oleic acid moiety in the molecule, e.g.,sucrose ester of cottonseed oil fatty acids, e.g., SEFA Cottonate.

First, sparge Phase A ingredients using nitrogen for approximately 15 minutes. Phase B ingredients are milled until the TiO$_2$ is homogeneously dispersed, and then added to Phase A. Phase C ingredients are then dispersed into Phase A/B until uniform using propeller type mixing and heated the mixture to about 75° C. In a separate vessel, Phase D ingredients are combined and heated to about 75° C. The mixture of phases A/B/C are then blanketed with a slow, steady stream of nitrogen. Next the Phase D ingredients are homogenized into the mixture of phases A/B/C using any rotor/stator type of homogenizer for approximately 15 minutes. After the 15 minutes, the mixing is switched to low rpm sweep mixing. Next, phase E ingredients are combined and added to the mixture of phases A–D. Once phase E is mixed and the batch mixture is homogeneous, the entire batch mixture is cooled. When the batch is cooled to about 50° C., phase F ingredients are added and homogenized. When the batch is cooled to about 40° C., phase G ingredients are added to the batch mixture. Lastly, when the batch mixture is cooled to about 30° C., the phase H ingredients are combined to the batch mixture. Mixing is continued until the batch mixture is uniform.

Apply the composition to a subjects facial skin at the rate of 2 mg composition/cm$^2$ skin to provide an essentially immediate visual improvement in skin appearance, e.g., reduced visibility of pores and a more even sldn tone. Apply the composition to a subject's face at the same rate once or twice daily for a period of 3–6 months, to improve skin surface texture, including diminishing fine lines and wrinkles, in addition to the essentially immediate improvements in appearance.

Examples 4–5

Oil-in-water emulsions are prepared from the following ingredients using conventional formulating techniques.

|         |                        | Ex 4    | Ex 5    |
|---------|------------------------|---------|---------|
| Phase A | distilled water        | qs 100  | qs 100  |
| Phase B | Glycerin               | 6       | 6       |
|         | TiO$_2$                | 0.75    | 0.75    |
| Phase C | Glycerin               | 3       | 3       |
|         | Carbopol 954           | 0.4     | 0.4     |
|         | EDTA                   | 0.1     | 0.1     |
| Phase D | Cetyl Palmitate        | 1.5     | 1.5     |
|         | Cetyl Alcohol          | 2.25    | 2.25    |
|         | Stearyl Alcohol        | 1.5     | 1.5     |
|         | Stearic Acid           | 0.31    | 0.31    |
|         | PEG-100 Stearate       | 0.31    | 0.31    |
|         | Silicone Wax DC2501    | 2       | 2       |
|         | DC 3225C               | 1.88    | 1.88    |
|         | Dimethicone 200/350cst | 0.63    | 0.63    |
|         | Tocopherol Acetate     | 0       | 0.5     |
|         | Niacinamide            | 2       | 2       |
| Phase E | distilled water        | 2       | 2       |
|         | NaOH                   | to neutralize Carbopol | to neutralize Carbopol |
| Phase F | D-Panthenol            | 0       | 0.5     |
|         | distilled water        | 0       | 5       |
| Phase G | Glydant PIus           | 0.1     | 0.1     |
|         | distilled water        | 1       | 1       |
|         | glycerin               | 1       | 1       |
| Phase H | Isopropyl Palmitate    | 1.25    | 1.25    |
|         | Retinol                | 0       | 0.04    |
|         | Tween 80               | 0       | 0.04    |
|         | BHT                    | 0       | 0.05    |

Prepare in the manner described for Examples 1–3.

Apply the composition to a subject's facial skin at the rate of 2 mg composition/cm$^2$ skln to provide an essentially immediate visual improvement in skin appearance, e.g., reduced visibility of pores and a more even skin tone. Apply the composition to a subject's face at the same rate once or twice daily for a period of 3–6 months, to improve skin surface texture, including diminishing fine lines and wrinkles, in addition to the essentially immediate improvements in appearance.

While particular embodiments of the subject invention have been described, it will be obvious to those skilled in the art that various changes and modifications to the subject invention can be made without departing from the spirit and scope of the invention. It is intended to cover, in the appended claims, all such modifications that are within the scope of the subject invention.

What is claimed:

1. A topical composition formed by combining components comprising:
    (a) from about 0.3% to about 2% by weight of the composition formed of pigmentary grade particulate material having a refractive index of at least about 2 and a neat primary particle size of from greater than 100 nm to about 300 nm; and
    (b) a topical carrier comprising from about 60% to about 99.7% by weight of the composition formed of a substantially liquid diluent;
the composition having a contrast ratio of from about 9 to about 30 and a % transmittance of from about 92% to about 62%.

2. The composition of claim 1 wherein the contrast ratio is from about 11 to about 22 and the % transmittance is from about 85% to about 75%.

3. The composition of claim 1 wherein the particulate material has a refractive index of from about 2 to about 3.

4. The composition of claim 1 wherein the particulate material comprises a material selected from the group consisting of $TiO_2$, ZnO, $ZrO_2$, and combinations thereof.

5. The composition of claim 1 wherein the total amount of all particulate material in the composition, by weight % of the composition, is about 10% or less.

6. The composition of claim 1 wherein the total amount of all particulate material in the composition, by weight % of the composition, is about 5% or less.

7. The composition of claim 1 wherein the total amount of all particulate material in the composition, by weight % of the composition, is about 3% or less.

8. The composition of claim 4 wherein the particulate material consists essentially of $TiO_2$.

9. The composition of claim 1 wherein the particulate material has a primary particle size when dispersed in the composition of from greater than 100 nm to about 1000 nm.

10. The composition of claim 1 having an apparent viscosity, in centipoise, of from about 5,000 to about 200,000.

11. The composition of claim 1 having an apparent viscosity, in centipoise, of from about 20,000 to about 150,000.

12. The composition of claim 1 having an apparent viscosity, in centipoise, of from about 25,000 to about 100,000.

13. The composition of claim 1 further comprising a skin conditioning component.

14. The composition of claim 1 further having a Hydration Factor of at least about 0.

15. A topical composition formed by combining components comprising:
   (a) from about 0.3% to about 2% by weight of the composition formed of a pigmentary grade particulate material selected from the group consisting of $TiO_2$, ZnO, $ZrO_2$, and combinations thereof, and having a neat primary particle size of from greater than 100 nm to about 300 nm; and
   (b) a topical carrier comprising from about 60% to about 99.7% by weight of the composition formed of a substantially liquid diluent;

wherein the particulate material has a primary particle size when dispersed in the composition of from greater than 100 nm to about 1000 nm and the composition has a contrast ratio of from about 9 to about 30, a % transmittance of from about 92% to about 62%, and an apparent viscosity, in centipoise, of from about 5,000 to about 200,000.

16. The composition of claim 15 wherein the total amount of all particulate material in the composition, by weight % of the composition, is about 10% or less.

17. The composition of claim 15 wherein the total amount of all particulate material in the composition, by weight % of the composition, is about 5% or less.

18. The composition of claim 15 wherein the total amount of all particulate material in the composition, by weight % of the composition, is about 3% or less.

19. The composition of claim 15 wherein the particulate material consists essentially of $TiO_2$.

20. The composition of claim 15 wherein the apparent viscosity is from about 20,000 to about 150,000 centipoise.

21. The composition of claim 15 wherein the apparent viscosity is from about 25,000 to about 100,000 centipoise.

22. A method of regulating skin condition comprising topically applying the composition of claim 1.

23. The method of claim 22 wherein regulating skin condition comprises masking imperfections on the skin surface.

* * * * *

UNITED STATES PATENT AND TRADEMARK OFFICE
CERTIFICATE OF CORRECTION

PATENT NO. : 5,972,359

DATED : October 26, 1999

INVENTOR(S) : Mark Richard Sine et al.

It is certified that error appears in the above-identified patent and that said Letters Patent is hereby corrected as shown below:

At column 6, line 51 "Technology 2nd" should read --Technology, 2nd--.

At column 7, line 39 "75%/," should read --75%,--.

At column 9, line 5 "Petrolatum which" should read --Petrolatum, which--.

At column 9, line 24 "acids including" should read --acids, including--.

At column 9, line 37 "mono-. di-" should read --mono-, di---.

At column 10, line 27 "as sed in" should read --as used in--.

At column 11, line 19 "a mire of" should read --a mixture of--.

At column 13, line 12 "allyl group" should read --alkyl group--.

At column 13, line 51 "$C_1$-$C_4$ 10 alkyl" should read --$C_1$-$C_4$ alkyl--.

At column 13, line 52 "R is" should read --$R^2$ is--.

At column 13, line 57 "the echain" should read --the chain--.

At column 14, line 21 "Polysorbate 20)" should read --(Polysorbate 20)--.

At column 14, line 60 "*Agents Their*" should read --*Agents, Their*--.

At column 15, line 4 for both occurrences "allyl" should read --alkyl--.

At column 15, line 35 "allyl-modified" should read --alkyl-modified--.

At column 15, line 50 "cyclic allyl" should read --cyclic alkyl--.

At column 16, line 37 "nonimiting" should read --nonlimiting--.

At column 16, line 66 "*Industry* vol." should read --*Industry*, vol.--.

At column 18, line 21 "—COOH and" should read ----COOH, and--.

At column 18, line 40 "$C_{14}$" should read --$C_{1-4}$--.

UNITED STATES PATENT AND TRADEMARK OFFICE
CERTIFICATE OF CORRECTION

PATENT NO. : 5,972,359

DATED : October 26, 1999

INVENTOR(S) : Mark Richard Sine et al.

It is certified that error appears in the above-identified patent and that said Letters Patent is hereby corrected as shown below:

At column 19, line 8 "CIO-30" should read --C10-30--.

At column 19, line 34 "(13)" should read --(B)--.

At column 19, line 38 "T" should read --1--.

At column 20, line 18 "crosslining" should read --crosslinking--.

At column 22, line 7 "SSS0OV" should read --SS500V--.

At column 22, line 58 "Crosskinked" should read --Crosslinked--.

At column 23, line 8 "Crosskinked" should read --Crosslinked--.

At column 23, line 17 "dialyl" should read --diallyl--.

At column 23, line 27 "ACP-1 120, ACP-1 179" should read --ACP-1120, ACP-1179--.

At column 24, line 23 "*Ed.* deNavarre" should read --*Ed.*, deNavarre--.

At column 24, line 48 "B3 compound" should read --$B_3$ compound--.

At column 25, line 58 "Company milwaukee" should read --Company (Milwaukee--.

At column 28, lines 63-64 "Commiphora particularly" should read --Commiphora, particularly--.

At column 29, line 7 "extract the" should read --extract, the--.

At column 29, lines 22-23 "(1972) discloses" should read --(1972), discloses--.

At column 29, line 62 "dihydroxy4" should read --dihydroxy-4--.

At column 30, line 7 "hydroxy4" should read --hydroxy-4--.

At column 30, line 30 "hydroxy4" should read --hydroxy-4--.

At column 31, line 39 "Hydroxv" should read --Hydroxy--.

At column 32, line 2 "sulfihydryl" should read --sulfhydryl--.

UNITED STATES PATENT AND TRADEMARK OFFICE
CERTIFICATE OF CORRECTION

PATENT NO.   : 5,972,359
DATED        : October 26, 1999
INVENTOR(S)  : Mark Richard Sine et al.

It is certified that error appears in the above-identified patent and that said Letters Patent is hereby corrected as shown below:

At column 32, line 32 "fled on" should read --filed on--.

At column 34, line 40 "thereof." should read --thereof.)--.

At column 35, line 49 "firm" should read --film--.

At column 36, line 38 "Comeometer" should read --Corneometer--.

At column 37, line 16 after "described" insert --herein, preferably a sucrose polyester in which the degree of esterification is 7-8, and in which the fatty acid moieties are C18 mono- and/or di-unsaturated and behenic, in a molar ratio of unsaturates:behenic of 1:7 to 3:5, more preferably the octaester of sucrose in which there are about 7 behenic fatty acid moieties and about 1 oleic acid moiety in the molecule, e.g., sucrose ester of cottonseed oil fatty acids, e.g., SEFA Cottonate.--.

At column 38, line 43 "on 5 the" should read --on the--.

At column 39, line 59 "subjects" should read --subject's--.

At column 39, line 62 "sldn" should read --skin--.

At column 40, line 34 "skln" should read --skin--.

Signed and Sealed this

Twenty-sixth Day of September, 2000

Attest:

Q. TODD DICKINSON

*Attesting Officer*   *Director of Patents and Trademarks*